US008623408B2

(12) United States Patent
Bodor

(10) Patent No.: US 8,623,408 B2
(45) Date of Patent: Jan. 7, 2014

(54) CLADRIBINE FORMULATIONS FOR IMPROVED ORAL AND TRANSMUCOSAL DELIVERY

(75) Inventor: Nicholas S Bodor, Bal Harbour, FL (US)

(73) Assignee: Ares Trading S.A., Aubonne (CH)

(*) Notice: Subject to any disclaimer, the term of this patent is extended or adjusted under 35 U.S.C. 154(b) by 0 days.

(21) Appl. No.: 12/891,492

(22) Filed: Sep. 27, 2010

(65) Prior Publication Data

US 2011/0015145 A1 Jan. 20, 2011

Related U.S. Application Data

(63) Continuation of application No. 10/551,094, filed as application No. PCT/US2004/009384 on Mar. 26, 2004, now abandoned.

(60) Provisional application No. 60/458,922, filed on Mar. 28, 2003, provisional application No. 60/484,756, filed on Jul. 2, 2003, provisional application No. 60/541,246, filed on Feb. 4, 2004.

(51) Int. Cl.
*A61K 9/20* (2006.01)
*A61K 9/14* (2006.01)
*A61K 31/52* (2006.01)
*A61K 31/715* (2006.01)

(52) U.S. Cl.
USPC ........ 424/464; 424/489; 514/58; 514/263.23; 514/825; 514/903; 514/908

(58) Field of Classification Search
USPC .............. 424/464, 489; 514/58, 263.23, 825, 514/903, 908
See application file for complete search history.

(56) References Cited

U.S. PATENT DOCUMENTS

| | | | |
|---|---|---|---|
| 3,459,731 A | 8/1969 | Gramera et al. |
| 4,226,848 A | 10/1980 | Nagai et al. |
| 4,250,163 A | 2/1981 | Nagai et al. |
| 4,383,992 A | 5/1983 | Lipari |
| 4,478,995 A | 10/1984 | Shinoda et al. |
| 4,497,803 A | 2/1985 | Harada et al. |
| 4,535,152 A | 8/1985 | Szejtli et al. |
| 4,596,795 A | 6/1986 | Pitha |
| 4,659,696 A | 4/1987 | Hirai et al. |
| 4,727,064 A | 2/1988 | Pitha |
| 4,764,604 A | 8/1988 | Müller |
| 4,870,060 A | 9/1989 | Müller |
| 5,106,837 A | 4/1992 | Carson et al. |
| 5,310,732 A | 5/1994 | Carson et al. |
| 5,401,724 A | 3/1995 | Beutler |
| 5,424,296 A | 6/1995 | Saven et al. |
| 5,506,214 A | 4/1996 | Beutler |
| 5,510,336 A | 4/1996 | Saven et al. |
| 6,194,395 B1 | 2/2001 | Schultz et al. |
| 6,239,118 B1 | 5/2001 | Schatz et al. |
| 6,407,079 B1 | 6/2002 | Müller et al. |
| 7,888,328 B2 * | 2/2011 | Bodor et al. ............ 514/46 |

FOREIGN PATENT DOCUMENTS

| | | |
|---|---|---|
| DE | 31 18 218 A1 | 4/1982 |
| DE | 33 17 064 A1 | 11/1984 |
| EP | 0 0940157 A1 | 11/1983 |
| EP | 0 149 197 B1 | 7/1985 |
| EP | 0 197 571 A2 | 10/1986 |
| GB | 2 189 245 A | 10/1987 |
| JP | 62-281855 | 12/1987 |
| JP | 01-287094 | 11/1989 |
| JP | 03-005438 | 1/1991 |
| JP | 10-265495 | 10/1998 |
| JP | 2002511073 A | 4/2002 |
| WO | 90/12035 A1 | 10/1990 |
| WO | WO 97/18839 A1 | 5/1997 |
| WO | WO 98/55148 A1 | 12/1998 |
| WO | WO 02/056915 A2 | 7/2002 |

OTHER PUBLICATIONS

F. Fawaz, F. Bonini, M. Guyot, J. Bildet, M. Maury and A.M. Lagueny, "Bioavailability of norfloxacin from PEG 6000 solid dispersion and cyclodextrin inclusion complexes in rabbits", International Journal of Pharmaceutics 132 (1996) 271 275.*
F. Veiga, C. Fernandes and F. Teixeira, "Oral bioavailability and hypoglycaemic activity of tolbutamide:cyclodextrin inclusion complexes", International Journal of Pharmaceutics 202 (2000) 165-171.*
Tomi Jarvinen, Kristiin Jarvinen, Nancy Schwarting and Valentino J. Stella, "Beta-Cyclodextrin Derivatives, SBE4-beta-CD and HP-beta-CD, Increase the Oral Bioavailability of Cinnarizine in Beagle Dogs", Journal of Pharmaceutical Sciences, vol. 84, No. 3, Mar. 1995, 295-299.*
Tarasiuk et al., "*Stability of 2-Chloro-2'-Deoxyadenosine at Various pH and Temperature*", Archivum Immunologiae et Therapiae Experimentalis, vol. 42, pp. 13-15, 1994, published by Birkhauser Publishers Ltd., Basel, Switzerland.
Romine et al., "*A Double-Blind, Placebo-Controlled, Randomized Trial of Cladribine in Relapsing-Remitting Multiple Sclerosis*", Proceedings of the Association of American Physicians, vol. 111, No. 1 pp. 35-44, 1999, published by Blackwell Publishing, Malden, MA.
Tortorella et al., Current Opinion on Investigational Drugs, 2(12), pp. 1751-1756, 2001, published by PharmaPress Ltd., London, GB.
Selby et al., "*Safety and Tolerability of Subcutaneous Cladribine Therapy in Progressive Multiple Sclerosis*", Can. J. Neurol Sci., vol. 25, pp. 295-299, 1998, published by Canadian Journal of Neurological Science, Calgary, Canada.
Rice et al., "*Cladribine and progressive MS Clinical and MRI outcomes of a multicenter controlled trial*", Neurology, vol. 54, pp. 1145-1155, 2000, published by Lippincott Williams and Wilkins, Hagerstown, MD.
Liliemark et al., "*On the Bioavailability of Oral and Subcutaneous 2-Chloro-2'-Deoxyadenosine in Humans: Alternative Routes of Administration*", Journal of Clinical Oncology, vol. 10, No. 10, pp. 1514-1518, 1992, published by American Society of Clinicial Oncology, Alexandria, VA.

(Continued)

*Primary Examiner* — Sue Liu
*Assistant Examiner* — Nathan W Schlientz
(74) *Attorney, Agent, or Firm* — Dentons US LLP

(57) ABSTRACT

Provided are compositions of cladribine and cyclodextrin which are especially suited for the oral and buccal administration of cladribine.

9 Claims, 6 Drawing Sheets

(56) References Cited

OTHER PUBLICATIONS

Karlsson et al., "*Oral cladribine for B-cell chronic lymphocytic leukaemia: report of a phase II trial with a 3-d, 3-weekly schedule in untreated and pretreated patients, and a long-term follow-up of 126 previously untreated patients*", British Journal of Haematology, vol. 116, pp. 538-548, 2002, published by Blackwell Science Ltd., Oxford, UK.

Liliemark, "*The Clinical Pharmacokinetics of Cladribine*" Clin. Pharmacokinet, vol. 32 (2), pp. 120-131, 1997, published by Adis International Limited, Wolters Kluwer Health, Yardley, PA.

Nogradi, "*Dimethyl-β-Cyclodextrin*", Drugs of the Future, vol. 9, No. 8, pp. 577-578, 1984, published by JR Prous SA Publishers, Barcelona, Spain.

Nakai et al., "*Effects of Grinding on the Physical and Chemical Properties of Crystalline Medicinals with Microcrystalline Cellulose V: Comparison with Tri-O-methyl-β-cyclodextrin Ground Mixtures*", Chem. Pharm. Bulletin, vol. 28(5), pp. 1552-1558, 1980, published by Pharmaceutical Society of Japan, Tokyo, Japan.

Saenger, "Clyclodextrin Inclusion Compounds in Research and Industry", Angew. Chem. Int. Ed. Engl., vol. 19, pp. 344-362, 1980, published by Verlag Chemie, GmbH, Weinheim, Germany.

Albertioni et al., "On the bioavailability of 2-chloro-2'-deoxyadenosine (CdA)", Eur J Clin Pharmacol., vol. 44, pp. 579-582, 1993, Springer-Verlag, Germany.

Ahn et al., "Chiral Recognition in Gas-Phase Cyclodextrin: Amino Acid Complexes-Is the Three Point Interaction Still Valid in the Gas Phase?", J Am Soc Mass Spectrom, vol. 12, pp. 278-287, 2001, Elsevier Science, Inc., US.

Bakthiar et al., "A study of the complexation between dimethyl-β-cyclodextrin and steroid hormones using electrospray ionization mass spectrometry", Rapid Communications in Mass Spectrometry, vol. 11, pp. 1478-1481, 1997, John Wiley and Sons Ltd, England.

Beutler et al., "The treatment of chronic progressive multiple sclerosis with cladribine", Proc. Natl. Acad. Sci. USA, Medical Sciences, vol. 93, pp. 1716-1720, 1996, National Academy of Sciences, US.

Cheng et al., "Measurement of chiral complexes of cyclodextrin and amino acids by electrospray ionization time-of-flight mass spectrometry", J. Mass Spectrom, vol. 36, pp. 834-836, 2001, John Wiley & Sons, Ltd., England.

Choi et al., "FT-Raman and FT-IR Spectra of the Non-steroidal Anti-inflammatory Drug Ketoprofen Included in Cyclodextrins", Analytical Sciences, vol. 17 Supplement, pp. i785-i788, 2001, The Japan Society for Analytical Chemistry, Japan.

Giordano et al., "Thermal analysis of cyclodextrins and their inclusion compounds", Thermochimica Acta 380, pp. 123-151, 2001, Elsevier Science B.V., The Netherlands.

Hwang et al., "Water Suppression That Works. Excitation Sculpting Using Arbitrary Waveforms and Pulsed Field Gradients", Journal of Magnetic Resonance, Series A, vol. 112, pp. 275-279, 1995, Academic Press, Inc., US.

Lamcharfi et al., "Electrospray Ionization Mass Spectrometry in Supramolecular Chemistry: Characterization of Non-covalent Cyclodextrin Complexes", Journal of Mass Spectrometry, vol. 31, pp. 982-986, 1996, John Wiley & Sons, Ltd., England.

Loftsson et al., "Pharmaceutical Applications of Cyclodextrin. 1. Drug Solubilization and Stabilization", Journal of Pharmaceutical Sciences, vol. 85, No. 10, pp. 1017-1025, 1996, American Pharmaceutical Association and the American Chemical Society, US.

Meier et al., "The Influence of β- and y-Cyclodextrin Cavity Size on the Association Constant with Decanoate and Octanoate Anions", Journal of Inclusion Phenomena and Macrocyclic Chemistry, vol. 40, pp. 291-295, 2001, Kluwer Academic Publishers, The Netherlands.

Mura et al., "Interactions of ketoprofen and ibuprofen with β-cyclodextrins in solution and in the solid state", International Journal of Pharmaceutics, vol. 166, pp. 189-203, 1998, Elsevier Science B.V., The Netherlands.

Nolan et al., "Preparation of Vesicles and Nanoparticles of Amphiphilic Cyclodextrins Containing Labile Disulfide Bonds", Langmuir, vol. 19, pp. 4469-4472, 2003, American Chemical Society, US.

Ramanathan et al., "Electrospray Ionization Mass Spectrometric Study of Encapsulation of Amino Acids by Cyclodextrins", J. Am Soc Mass Spectrom, vol. 6, pp. 866-871, 1995, American Society for Mass Spectrometry, US.

Redenti et al., "Raman and Solid State $^{13}$C-NMR Investigation of the Structure of the 1 : 1 Amorphous Piroxicam : β-Cyclodextrin Inclusion Compound", Biospectroscopy, vol. 5, pp. 243-251, 1999, John Wiley & Sons, Inc., US.

Sipe et al., "Cladribine in treatment of chronic progressive multiple sclerosis", The Lancet, vol. 344, pp. 9-13, 1994, Lancet Publishing Group, England.

Szejtli, "Introduction and General Overview of Cyclodextrin Chemistry", Chem. Rev., vol. 98, pp. 1743-1753, 1998, American Chemical Society, US.

Uekama et al., "Cyclodextrin Drug Carrier Systems", Chem. Rev., vol. 98, pp. 2045-2076, 1998, American Chemical Society, US.

Uekama et al., "Peracylated β-Cyclodextrins as Novel Sustained-release Carriers for a Water-soluble Drug, Molsidomine", J. Pharm. Pharmacol., vol. 46, pp. 714-717, 1994, Pharmaceutical Press, England.

Taddei et al., "Influence of Environment on Piroxicam Polymorphism: Vibrational Spectroscopic Study", Biopolymers (Biospectroscopy), vol. 62, pp. 68-78, 2001, John Wiley & Sons, Inc., US.

International Search Report for PCT/US2004/009384, issued Dec. 2, 2004.

Van Axel Castelli et al., "Characterisation of an Inclusion Complex Between Cladribine and 2-Hydroxypropyl-62 -Cyclodextrin" Journal of Pharmaceutical Sciences, 2008, pp. 3897-3906, vol. 97, No. 9, Wiley Intersciences and the American Pharmacists Association, US.

* cited by examiner

CLADRIBINE FORMULATIONS FOR IMPROVED ORAL AND TRANSMUCOSAL DELIVERY

CROSS-REFERENCE TO EARLIER APPLICATIONS

This application is a continuation of prior U.S. application Ser. No. 10/551,094 filed Aug. 4, 2006, now abandoned, which is the U.S. national stage of International Application No. PCT/US2004/009384, filed Mar. 26, 2004, which claims benefit under 35 U.S.C. §119(e) of U.S. Provisional Application No. 60/458,922, filed Mar. 28, 2003; of U.S. Provisional Application No. 60/484,756, filed Jul. 2, 2003; and of U.S. Provisional Application No. 60/541,246, filed Feb. 4, 2004, all of said applications being hereby incorporated by reference herein in their entireties and relied upon.

FIELD OF THE INVENTION

The invention relates to a composition comprising a cladribine-cyclodextrin complex formulated into a solid oral dosage form or a transmucosal dosage form and to a method for enhancing the oral and transmucosal bioavailability of cladribine.

BACKGROUND OF THE INVENTION

Cladribine, which is an acid-labile drug, has the chemical structure as set forth below:

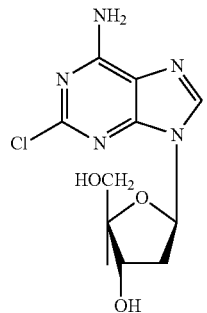

It is also known as 2-chloro-2'-deoxyadenosine or 2-CdA.

Cladribine is an antimetabolite which has use in the treatment of lymphoproliferative disorders. It has been used to treat experimental leukemias such as L1210 and clinically for hairy cell leukemia and chronic lymphocytic leukemia as well as Waldenstrom's macroglobulinaemia. It has also been used as an immunosuppressive agent and as a modality for the treatment of a variety of autoimmune conditions including rheumatoid arthritis, inflammatory bowel disease (e.g., Crohn's disease, ulcerative colitis) and multiple sclerosis (see e.g., J. Liliemark, *Clin. Pharmacokinet*, 32(2): 120-131, 1997). It has also been investigated, either experimentally or clinically in, for example, lymphomas, Langerhan's cell histiocytosis, lupus erythematosus, chronic plaque psoriasis, Sezary syndrome, Bing-Neel syndrome, recurrent glioma, and solid tumors.

Oral delivery of drugs is often preferred to parenteral delivery for a variety of reasons, foremost patient compliance, or for cost or therapeutic considerations. Patient compliance is enhanced insofar as oral dosage forms alleviate repeated health care provider visits, or the discomfort of injections or prolonged infusion times associated with some active drugs. At a time of escalating health care costs, the reduced costs associated with oral or transmucosal administration versus parenteral administration costs gain importance. The cost of parenteral administration is much higher due to the requirement that a health care professional administer the cladribine in the health care provider setting, which also includes all attendant costs associated with such administration. Furthermore, in certain instances, therapeutic considerations such as the need for a slow release of cladribine over a prolonged period of time may be practically met only by oral or transmucosal delivery.

However, to date the oral and transmucosal delivery of cladribine has been plagued by low bioavailability (see, e.g., J. Liliemark et al., *J. Clin. Oncol.*, 10(10): 1514-1518, 1992), and suboptimal interpatient variation (see, e.g., J. Liliemark, *Clin. Pharmacokinet*, 32 (2): 120-131, 1997). See also, A. Tarasuik, et al. reporting poor absorption and pH dependent lability (*Arch. Immunal. et Therapiae Exper.*, 42: 13-15, 1994).

Cyclodextrins are cyclic oligosaccharides composed of cyclic α-(1→4) linked D-glucopyranose units. Cyclodextrins with six to eight units have been named α-, β- and γ-cyclodextrin, respectively. The number of units determines the size of the cone-shaped cavity which characterizes cyclodextrins and into which drugs may include to form stable complexes. A number of derivatives of α-, β- and γ-cyclodextrin are known in which one or more hydroxyl groups is/are replaced with ether groups or other radicals. These compounds are thus known complexing agents and have been previously used in the pharmaceutical field to form inclusion complexes with water-insoluble drugs and to thus solubilize them in aqueous media.

Recently, Schultz et al., in U.S. Pat. No. 6,194,395 B1, have described complexing and solubilizing cladribine with cyclodextrin. The Schultz et al. patent primarily addresses the problems inherent in previously described aqueous formulations of cladribine, particularly for subcutaneous and intramuscular injection. Schultz et al. have found that cladribine is not only significantly more soluble in aqueous media when formulated with cyclodextrin, but also is more stable against acid-catalyzed hydrolysis when combined with cyclodextrin. The latter finding is taught to be of particular benefit in the formulation of solid oral dosage forms, where the compound would normally undergo hydrolysis in the acid pH of the stomach contents. Schultz et al. do not appear to have described any actual work in connection with solid oral dosage forms. In fact, they describe only one method of preparing the solid dosage form, which is a melt extrusion process, in which the cladribine and cyclodextrin are mixed with other optional additives and then heated until melting occurs. Furthermore, the broad dosage ranges of 1 mg to 15 mg of cladribine and 100 mg to 500 mg of cyclodextrin listed in the patent suggest no criticality to the particular amount of cyclodextrin to be present with a given amount of cladribine in a solid oral dosage form. Indeed, these dosage ranges include many combinations which may be suitable as mixtures but not for complex formation. For example, a ratio of 1 mg of cladribine to 500 mg of cyclodextrin contains too much cyclodextrin, so that the drug would not readily leave the complex and achieve its therapeutic function. On the other hand, 15 mg of cladribine and only 100 mg of cyclodextrin would not be enough to complex that amount of cladribine.

The Schultz et al. patent does suggest improving the stability of cladribine in oral dosage forms by combining/complexing it with cyclodextrin, but does not suggest improving the drug's oral bioavailability by such means; in fact, the patent does not describe or suggest a method for enhancing or maximizing the bioavailability of cladribine from a solid oral dosage form of cladribine and cyclodextrin, or a composition specially designed to do so. Further, Schultz et al. do not suggest cladribine/cyclodextrin combinations for transmucosal administration, that is, in a form intended for administration through the mucosa lining the nasal, oral, vaginal or rectal cavities rather than via the orogastric route, much less enhancing the bioavailability of the drug when administered via such a dosage form.

Many workers have studied the solubility of specific drugs in water containing various concentrations of selected cyclodextrins in order to demonstrate that increasing concentrations of cyclodextrins increase the solubility of the drugs at selected temperatures and pH levels, as for example reported in the Schultz et al., patent. Phase solubility studies have also been performed by various workers in order to elucidate the nature of the complex formation, for example, whether the cyclodextrin and drug form a 1:1 complex or a 1:2 complex; see, for example, Harada et al. U.S. Pat. No. 4,497,803, relating to inclusion complexes of lankacidin-group antibiotics with cyclodextrin, and Shinoda at al. U.S. Pat. No. 4,478,995, relating to a complex of an acid addition salt of (2'-benzyloxycarbonyl)phenyl trans-4-guanidinomethylcyclohexanecarboxylate with a cyclodextrin.

It has been a common practice in the pharmaceutical arts to use a surplus of cyclodextrin in solid dosage forms in which the cyclodextrin is used to improve drug solubilization, unless the solubility is such that excess cyclodextrin would result in too large a dosage form. Conventional wisdom would dictate that for a solid oral dosage form, especially of an acid-labile drug such as cladribine, excess cyclodextrin would be expected to protect the drug in the acid environment of the stomach and, ideally, deliver it through the gut wall/gastric mucosa still protected as a complex with the cyclodextrin. In the bloodstream, away from the deleterious influence of stomach acid, the drug would then be expected to dissociate from the complex and perform its therapeutic function.

While Schultz et al. teach that a cladribine-cyclodextrin complex improves the water solubility and acid stability of cladribine, the art does not suggest how to maximize or enhance the benefits of the complexation in terms of bioavailability and interpatient variation when the complex is to be administered in a solid oral dosage form or a transmucosal dosage form.

SUMMARY OF THE INVENTION

It has now been found that excess cyclodextrin inhibits the absorption of cladribine from a solid oral dosage form or a transmucosal dosage form comprising a cladribine-cyclodextrin complex, and that a solid oral or a transmucosal dosage form of a saturated cladribine-cyclodextrin complex improves oral and/or transmucosal bioavailability and/or achieves lower interpatient and/or intrapatient variation of the drug.

The present invention provides a pharmaceutical composition comprising a saturated cladribine-cyclodextrin complex formulated into a solid oral dosage form or a transmucosal dosage form which is substantially free of cyclodextrin in excess of the minimum amount needed to maximize the amount of cladribine in the complex. In a particular aspect of the invention, the pharmaceutical composition comprises a saturated cladribine-cyclodextrin complex formulated into a solid oral dosage form or a transmucosal dosage form which is substantially free of cyclodextrin in excess of the minimum amount needed to maintain substantially all of the cladribine in the complex. This composition provides cladribine in its highest thermodynamic activity state at the time it contacts the gastric mucosa (in the case of an oral dosage form) or the rectal, vaginal, buccal or nasal mucosa (in the case of transmucosal dosage forms).

The invention also provides a method for increasing the oral or transmucosal bioavailability of cladribine comprising administering to a subject in need thereof, a pharmaceutical composition comprising a saturated cladribine-cyclodextrin complex formulated into a solid oral dosage form or a transmucosal dosage form which is substantially free of cyclodextrin in excess of the minimum amount needed to maximize the amount of the cladribine in the complex. In a particular aspect of the method, the composition administered comprises a saturated cladribine-cyclodextrin complex formulated into a solid oral dosage form or a transmucosal dosage form which is substantially free of cyclodextrin in excess of the minimum amount needed to maintain substantially all of the cladribine in the complex.

The invention further provides a method for enhancing the bioavailability of cladribine from a solid oral dosage form or a transmucosal dosage form in a mammal in need of treatment with cladribine, the method comprising: (a) determining the minimum amount of cyclodextrin required to complex with a selected amount of cladribine and to maintain said selected amount of cladribine in the complex; (b) combining an amount of cladribine in excess of said selected amount with said minimum amount of cyclodextrin in an aqueous medium; (c) removing uncomplexed cladribine from the complexation medium; (d) removing water from the resultant solution to afford the dry saturated cladribine-cyclodextrin complex; (e) formulating said dry saturated cladribine-cyclodextrin complex into a solid oral dosage form or a transmucosal dosage form substantially free of cyclodextrin in excess of the minimum amount required to maximize the amount of cladribine in the complex; and (f) administering the dosage form orally or transmucosally to the mammal. In a particular aspect of this method, step (e) comprises formulating said dry saturated cladribine-cyclodextrin complex into a solid oral dosage form or a transmucosal dosage form substantially free of cyclodextrin in excess of the minimum amount required to maintain substantially all of the cladribine in the complex.

The invention further provides for treatment of conditions responsive to administration of cladribine in mammals by administering thereto the composition of the invention. Use of cladribine in the preparation of the pharmaceutical compositions of the invention for administration to treat symptoms of cladribine-responsive conditions and for enhancing the oral or transmucosal bioavailability of cladribine is also provided.

In one particular embodiment, the invention provides a novel 1:2 complex of cladribine:γ-cyclodextrin which is particularly advantageous. In a related embodiment, there is provided a mixture of a 1:1 cladribine:γ-cyclodextrin complex and a 1:2 cladribine:γ-cyclodextrin complex, wherein the 1:2 complex is predominant.

BRIEF DESCRIPTION OF THE DRAWINGS

A more complete appreciation of the invention and its many attendant advantages will be readily understood by reference to the following detailed description and the accompanying drawings, wherein.

DETAILED DESCRIPTION OF THE INVENTION

Figure 1:
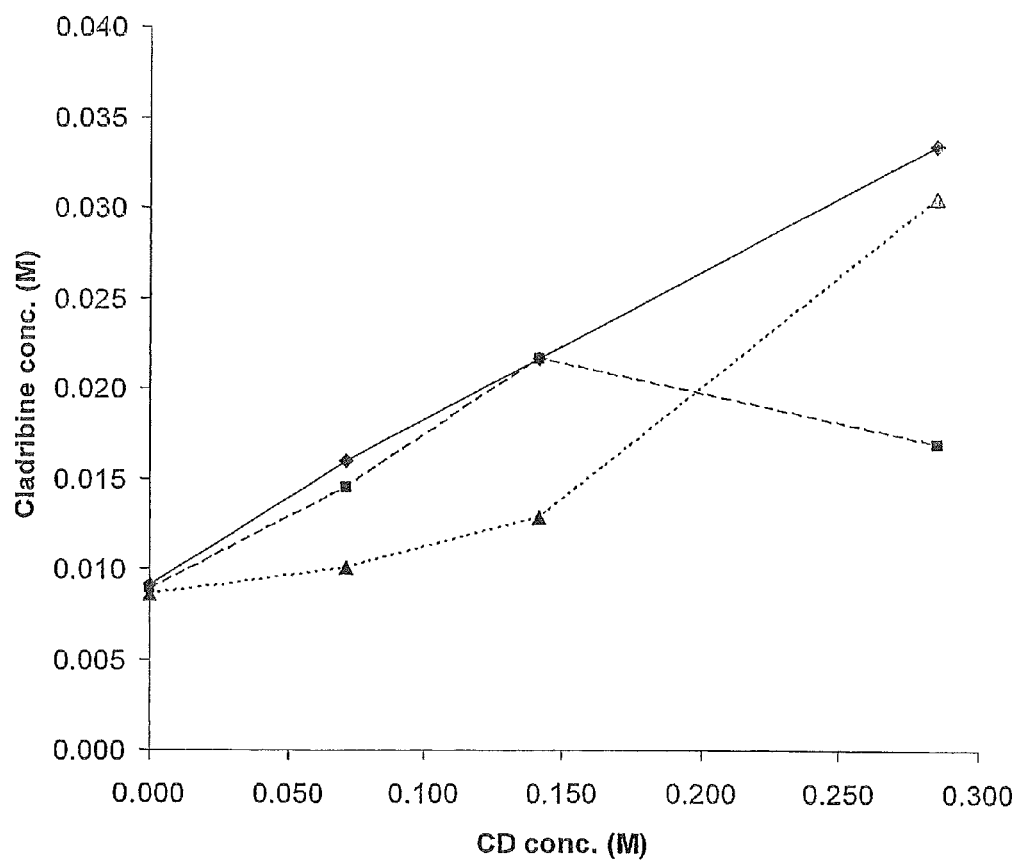
FIG. 1 is a graphical representation of the results of phase solubility studies, where various cyclodextrin (CD) molar concentrations are plotted against various cladribine molar concentrations, with (♦) representing hydroxypropyl-β-cyclodextrin, (■) representing hydroxypropyl-β-cyclodextrin with added hydroxypropyl methylcellulose, and (▲) representing γ-cyclodextrin.

Throughout the instant specification and claims, the following definitions and general statements are applicable.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The term "complex" as used herein means an inclusion complex, in which the hydrophobic portion of the cladribine molecule (the nitrogen-containing ring system) is inserted into the hydrophobic cavity of the cyclodextrin molecule.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" or have a partially closed meaning, that is, they do not permit inclusion of steps or features or components which would substantially change the essential characteristics of a process or composition; for example, steps or features or components which would significantly interfere with the desired properties of the compositions described herein, i.e., the process or composition is limited to the specified steps or materials and those which do not materially affect the basic and novel characteristics of the invention. The basic and novel features herein are the provision of a saturated cladribine-cyclodextrin complex in a solid oral dosage form or a transmucosal dosage form which is substantially free of cyclodextrin in excess of the minimum amount required to maximize the amount of cladribine in the complex, so as to provide improved bioavailability and/or lower interpatient variation following administration. In a particular embodiment of the invention, the basic and novel features herein are the provision of a saturated cladribine-cyclodextrin complex in a solid oral dosage form or a transmucosal dosage form which is substantially free of cyclodextrin in excess of the minimum amount required to maintain substantially all of the cladribine in the complex, providing particularly enhanced bioavailability and/or low interpatient and/or low intrapatient variability following administration.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

The term "saturated" when used in conjunction with a complex of cladribine in cyclodextrin means that the complex is saturated with cladribine, that is, the complex contains the maximum amount of cladribine which can be complexed with a given amount of cyclodextrin under the conditions of complexation used. A phase solubility study can be used to provide this information, as described in more detail hereinafter. (Conditions for the complexation are also described in more detail below.) Alternatively, a saturated complex may be arrived at empirically by simply adding cladribine to an aqueous solution of the selected cyclodextrin until a precipitate (of uncomplexed cladribine) forms; ultimately, the precipitate is removed and the solution lyophilized to provide the dry saturated complex.

The expression "substantially", as in "substantially free" or "substantially all", means within 20% of the exact calculated amount. In the case of the expression "substantially free of cyclodextrin in excess of the minimum amount needed to maintain substantially all of the cladribine in the complex," the minimum amount of cyclodextrin needed to maintain the cladribine in the complex can be obtained from phase solubility studies as explained in more detail below. The actual amount of cyclodextrin should be within 20% of that minimum, plus or minus, preferably within 10% of that minimum, plus or minus, even more preferably within 5% of that minimum, plus or minus, and should maintain at least 90% or more, preferably at least 95% or more, of the drug in the complex. On the other hand, when the expression "substantially free of cyclodextrin in excess of the minimum amount needed to maximize the amount of cladribine in the complex" is used, less than the aforenoted amount of cyclodextrin may be utilized and a larger amount of cladribine may be present in the dosage form in uncomplexed form as a result. This may occur by using a less concentrated cyclodextrin solution for the complexation reaction and/or by conducting the complexation at the upper end of the temperature range suggested below. It is considered particularly advantageous, however, to use enough cyclodextrin to maintain substantially all of the cladribine in the complex, and to thus minimize the amount of uncomplexed cladribine in the dosage form.

The term "interpatient variability" refers to variation among patients to which a drug is administered. The term "intrapatient variability" refers to variation experienced by a single patient when dosed at different times.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001).

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations have not been described in detail, in order not to unnecessarily obscure the present invention.

There is provided by the present invention compositions, as well as methods of making and of using pharmaceutical compositions, useful to achieve desirable pharmacokinetic properties. Such compositions stem from the discovery that solutions of cyclodextrin and cladribine in which cladribine is in its highest thermodynamic state, when presented to the mucosa through which they are absorbed (gastric, nasal, rectal, buccal, sublingual or vaginal) are associated with improved cladribine absorption, as reflected by higher bioavailability and/or lower interpatient variation.

It is postulated, without wishing to so limit the invention, that upon dissolution (e.g., by contact with a fluid, such as a bodily fluid), dry compositions of a saturated cladribine-cyclodextrin complex not containing excess cyclodextrin form a locally saturated cladribine solution in which cladribine is in the state of highest thermodynamic activity (HTA), thus favoring absorption. Cladribine has a fairly low, although not insignificant, intrinsic aqueous solubility. The free cladribine formed from dissociation of the complex in a saturated aqueous solution seeks a more stable activity level, and if excess cyclodextrin were present, the cladribine would seek greater stability by re-complexing with the cyclodextrin. By controlling the amount of cyclodextrin so that the dosage form is substantially free of cyclodextrin in excess of the amount needed to keep the cladribine in the complex, it will not be easy for the cladribine in the locally saturated solution to recombine with cyclodextrin. Therefore, this cladribine will seek a state of lower thermodynamic activity/greater stability by being absorbed through the gastric musoca (in the case of a solid oral dosage form) or through the nasal, buccal, vaginal or rectal mucosa (in the case of a transmucosal dosage form). This approach is shown hereinafter inter alia to increase bioavailability, likely by avoiding or minimizing the inhibition of cladribine absorption which would result from the presence of excess cyclodextrin. In the presence of a large amount of excess cyclodextrin, the cladribine in solution would be expected to recombine with cyclodextrin. This will not achieve optimum bioavailability, because it is essential that the cladribine move out of the complex in which it is encapsulated if the drug is to accomplish its therapeutic function.

In view of the foregoing, it is apparent that to produce optimal pharmaceutical compositions, in a solid oral or a transmucosal dosage form, these dosage forms should be formulated to release a localized saturated cladribine solution, upon contact of the solid dosage forms with body fluid at the mucosa, in which cladribine is in its HTA state. To provide such a localized saturated solution in vivo, it is important to first identify the optimal ratio of cladribine to cyclodextrin, which ratio is referred to herein as the HTA ratio, to be used in the solid dosage form. In the case of a buccal dosage form, a highly concentrated solution made by dissolving the saturated complex in a minimal amount of water and placing this solution in the buccal cavity can accomplish the same effect.

The HTA ratio is empirically determined and is identified as the ratio of cladribine to a specific cyclodextrin which corresponds to the maximum amount of cladribine that can be complexed with a given amount of cyclodextrin. The HTA ratio may be determined using an empirical method such as a phase solubility study to determine the saturation concentration of cladribine that can be solubilized with different concentrations of cyclodextrin solutions. Hence, the method identifies the concentrations at which a saturated cladribine-cyclodextrin complex is formed. It is noted that the molar ratio represented by a point on the phase solubility graph shows how many moles of cyclodextrin are the minimum needed to maintain the drug in the complex, under given conditions; this may then be converted to a weight ratio. For example, if a phase solubility diagram shows that 9 moles of a given cyclodextrin are needed to maintain substantially all of the cladribine in a saturated complex, then multiplying the number of moles of cladribine by its molecular weight and multiplying the number of moles the cyclodextrin by its molecular weight, one can arrive at the ratio of the products as an appropriate optimized weight ratio. A phase solubility study also provides information about the nature of the cladribine-cyclodextrin complex formed, for example whether the complex is a 1:1 complex (1 molecule of drug complexed with 1 molecule of cyclodextrin) or a 1:2 complex (1 molecule of drug complexed with 2 molecules of cyclodextrin).

In accordance with the present invention, one can start using either cyclodextrin or cladribine as the fixed variable to which an excess of the other is added to identify various HTA data points (indicating saturated cladribine-cyclodextrin complexes) and draw the resultant HTA line. Typically, cladribine is added to an aqueous solution having a known concentration of cyclodextrin under conditions empirically found to promote complex formation. A concentrated solution, for example, of approximately 27% for γ-cyclodextrin and approximately 40% for hydroxypropyl-β-cyclodextrin, is in one embodiment particularly advantageous. Generally, the complexation is conducted at room temperature or with slight heating (up to about 50° C. or even up to 60° C.). Excess cladribine, if any, is then removed and the cladribine concentration in the complex is subsequently measured. The concentration measured represents the cladribine saturation concentration for the given cyclodextrin concentration. This process is repeated for a different known concentration of cyclodextrin until several data points are obtained. Each data point represents the saturated concentration of the cladribine dissolved in a known concentration of cyclodextrin. The data points are then plotted to show the saturated concentration of cladribine against the various cyclodextrin concentrations used. The graph is a phase solubility diagram which can be used to determine the saturation amount of cladribine for any specific concentration of cyclodextrin used to form a saturated cladribine-cyclodextrin complex under a given set of complexation conditions.

One of skill in the art will appreciate that concentrations at which saturated cladribine-cyclodextrin complexes are formed (and thus HTA ratios as well) may be identified by a variety of alternative methodologies. Accordingly, any method known in the field suitable to identify these concentrations is within the scope of the invention.

It has been discovered that desirable pharmacological properties (improved bioavailability and/or lower interpatient and/or intrapatient variation) are associated with the inclusion complexes of this invention.

The cyclodextrins within the scope of this invention include the natural cyclodextrins α-, β-, and γ-cyclodextrin, and derivatives thereof, in particular, derivatives wherein one or more of the hydroxy groups are substituted, for example, by alkyl, hydroxyalkyl, carboxyalkyl, alkylcarbonyl, carboxyalkoxyalkyl, alkylcarbonyloxyalkyl, alkoxycarbonylalkyl or hydroxy-(mono or polyalkoxy)alkyl groups; and wherein each alkyl or alkylene moiety preferably contains up to six carbons. Substituted cyclodextrins can generally be obtained in varying degrees of substitution, for example, from 1 to 14, preferably from 4 to 7; the degree of substitution is the approximate average number of substituent groups on the cyclodextrin molecule, for example, the approximate number of hydroxypropyl groups in the case of the hydroxypropyl-β-cyclodextrin molecule, and all such variations are within the ambit of this invention. Substituted cyclodextrins which can be used in the invention include polyethers, for example, as described in U.S. Pat. No. 3,459,731. Further examples of substituted cyclodextrins include ethers wherein the hydrogen of one or more cyclodextrin hydroxy groups is replaced by $C_{1-6}$ alkyl, hydroxy-$C_{1-6}$ alkyl, carboxy-$C_{1-6}$ alkyl or $C_{1-6}$ alkyloxycarbonyl-$C_{1-6}$ alkyl groups or mixed ethers thereof. In particular, such substituted cyclodextrins are ethers wherein the hydrogen of one or more cyclodextrin hydroxy groups is replaced by $C_{1-3}$ alkyl, hydroxy-$C_{2-4}$ alkyl or carboxy-$C_{1-2}$ alkyl or more particularly by methyl, ethyl, hydroxyethyl, hydroxypropyl, hydroxybutyl, carboxymethyl or carboxyethyl. The term "$C_{1-6}$ alkyl" is meant to include straight and branched saturated hydrocarbon radicals, having from 1 to 6 carbon atoms such as methyl, ethyl, 1-methylethyl, 1,1-dimethylethyl, propyl, 2-methylpropyl, butyl, pentyl, hexyl and the like. Other cyclodextrins contemplated for use herein include glucosyl-β-cyclodextrin and maltosyl-β-cyclodextrin. Of particular utility in the present invention are the β-cyclodextrin ethers such as dimethyl-β-cyclodextrin as described in *Cyclodextrins of the Future*, Vol. 9, No. 8, p. 577-578 by M. Nogradi (1984), randomly methylated β-cyclodextrin and polyethers such as hydroxypropyl-β-cyclodextrin, hydroxyethyl-β-cyclodextrin, hydroxypropyl-γ-cyclodextrin, and hydroxyethyl-γ-cyclodextrin, as well as sulfobutyl ethers, especially β-cyclodextrin sulfobutyl ether. In addition to simple cyclodextrins, branched cyclodextrins and cyclodextrin polymers may also be used. Other cyclodextrins are described, for example, in *Chemical and Pharmaceutical Bulletin* 28: 1552-1558 (1980); Yakugyo Jiho No. 6452 (28 Mar. 1983); *Angew. Chem. Int. Ed. Engl.* 19: 344-362 (1980); U.S. Pat. Nos. 3,459,731 and 4,535,152; European Patent Nos. EP 0 149 197A and EP 0 197 571A; PCT International Patent Publication No. WO90/12035; and UK Patent Publication GB 2,189,245. Other references describing cyclodextrins for use in the compositions according to the present invention, and which provide a guide for the preparation, purification and analysis of cyclodextrins include the following: *Cyclodextrin Technology* by Jozsef Szejtli, Kluwer Academic Publishers (1988) in the chapter Cyclodextrins in Pharmaceuticals; *Cyclodextrin Chemistry* by M. L. Bender et. al., Springer-Verlag, Berlin (1978); *Advances in Carbohydrate Chemistry*, Vol. 12, Ed. by M. L. Wolfram, Academic Press, New York in the chapter "The Schardinger Dextrins" by Dexter French, pp. 189-260; *Cyclodextrins and their Inclusion Complexes* by J. Szejtli, Akademiai Kiado, Budapest, Hungary (1982); I. Tabushi, *Acc. Chem. Research,* 1982, 15, pp. 66-72; W. Sanger, *Angewandte Chemie,* 92, p. 343-361 (1981); A. P. Croft et. al., *Tetrahedron,* 39, pp. 1417-1474 (1983); Irie et. al., *Pharmaceutical Research,* 5, pp. 713-716 (1988); Pitha et. al., *Int. J. Pharm.* 29, 73 (1986); U.S. Pat. Nos. 4,659,696 and 4,383,992; German Patent Nos. DE 3,118,218 and DE-3,317,064; and European Patent No. EP 0 094 157A. Patents describing hydroxyalkylated derivative of β- and γ-cyclodextrin include Pitha U.S. Pat. Nos. 4,596,795 and 4,727,064, Müller U.S. Pat. Nos. 4,764,604 4,870,060 and Müller et al., U.S. Pat. No. 6,407,079.

Cyclodextrins of particular interest for complexation with cladribine include: γ-cyclodextrin; hydroxyalkyl, e.g. hydroxyethyl or hydroxypropyl, derivatives of β- and γ-cyclodextrin; carboxyalkyl, e.g. carboxymethyl or carboxyethyl, derivatives of β- or γ-cyclodextrin; β-cyclodextrin sulfobutyl ether; dimethyl-β-cyclodextrin; and randomly methylated β-cyclodextrin. 2-Hydroxypropyl-β-cyclodextrin (HPβCD), 2-hydroxypropyl-γ-cyclodextrin (HPγCD), randomly methylated β-cyclodextrin, dimethyl-β-cyclodextrin, β-cyclodextrin sulfobutyl ether, carboxymethyl-β-cyclodextrin (CMβCD), carboxymethyl-γ-cyclodextrin (CMγCD) and γ-cyclodextrin (γCD) itself are of special interest, especially γ-cyclodextrin and hydroxypropyl-β-cyclodextrin, most especially γ-cyclodextrin.

Compositions of a saturated cladribine-cyclodextrin complex for use in the present invention can be prepared under conditions favoring complex formation in a liquid environment as described and as exemplified herein. The resultant liquid preparations can be subsequently converted to a dry form suitable for administration as a solid oral or transmucosal dosage form.

One of skill will appreciate that a variety of approaches are available in the field to prepare compositions as described herein. One available method exemplified herein includes the steps of mixing the cladribine in an aqueous cyclodextrin solution, maintaining the complexation medium at room temperature, with stirring, for from about 6 to about 24 hours, that is, for a sufficient time to achieve equilibrium, separating un-complexed cladribine, if any (e.g., by filtering or centrifugation), and lyophilizing or freeze-drying the saturated solution to form a solid saturated cladribine-cyclodextrin complex mixture.

Freeze-drying, also known as lyophilization, consists of three basic stages: first a freezing stage, then a primary drying stage and finally a secondary drying stage. EXAMPLE 2 below provides details of lyophilization as conducted on the batches described therein. This procedure can be further optimized by following the principles described by Xiaolin (Charlie) Tang and Michael J. Pikal in *Pharmaceutical Research*, Vol. 21, No. 2, February 2004, 191-200, incorporated by reference herein in its entirety and relied upon.

Pharmaceutical compositions according to the invention may optionally include one or more excipients or other pharmaceutically inert components. One of the advantages of the invention, however, is that cladribine drug forms as described herein can be prepared with the minimal amount of excipients necessary for shaping and producing the particular form, such as a tablet or patch. Excipients may be chosen from those that do not interfere with cladribine, with cyclodextrin or with complex formation.

Dosage forms are optionally formulated in a pharmaceutically acceptable vehicle with any of the well-known pharmaceutically acceptable carriers, diluents, binders, lubricants, disintegrants, scavengers, flavoring agents, coloring agents, and excipients (see *Handbook of Pharmaceutical Excipients*, Marcel Dekker Inc., New York and Basel (1998); Lachman et al. Eds., *The Theory and Practice of Industrial Pharmacy*, 3$^{rd}$ Ed., (1986); Lieberman et al., Eds. *Pharmaceutical Dosage Forms*, Marcel Dekker Inc., New York and Basel (1989); and *The Handbook of Pharmaceutical Excipients*, 3$^{rd}$ Ed., American Pharmaceutical Association and Pharmaceutical Press, 2000); see also *Remington's Pharmaceutical Sciences*, 18th Ed., Gennaro, Mack Publishing Co., Easton, Pa. (1990) and *Remington: The Science and Practice of Pharmacy*, Lippincott, Williams & Wilkins, (1995)). A simple solid oral or transmucosal dosage form consists of the saturated cladribine-cyclodextrin complex compressed with a small amount (e.g. about 1% by weight) of a suitable binder or lubricant such as magnesium stearate.

In particular embodiments, the saturated cladribine-cyclodextrin complex is used for the transmucosal or the oral administration of cladribine.

As used herein, "mucosa" means the epithelial membranes lining the nasal, oral, vaginal and rectal cavities, as well as those lining the stomach (the gastric mucosa). As used herein, mucosal and transmucosal are used interchangeably. Transmucosal delivery methods and forms are well-known in the art. These include buccal and sublingual tablets, lozenges, adhesive patches, gels, solutions or sprays (powder, liquid or aerosol), and suppositories or foams (for rectal or vaginal administration). Transmucosal delivery methods and forms do not include the methods and forms for oral use, which are intended to be swallowed and are simply called oral dosage forms herein, despite the fact that they ultimately deliver the drug through the gastric mucosa. When the transmucosal form is a liquid, it can be obtained by dissolving the saturated complex in a minimum amount of water, for example 500 mg of the saturated complex with HPβCD in 0.5 ml water (50% w/w solution), or 500 mg of the saturated γCD complex in 1.0 ml of water. A few drops of such a solution can be inserted into the buccal cavity and retained there for about 2 minutes to allow for absorption through the buccal mucosa. Nevertheless, solid transmucosal dosage forms are generally preferred over liquid forms.

In certain instances, oral or mucosal absorption may be further facilitated by the addition of various excipients and additives to increase solubility or to enhance penetration, such as by the modification of the microenvironment, or by the addition of mucoadhesive excipients to improve contact between the delivery system and the mucosal tissue.

Buccal drug delivery can be effected by placing the buccal dosage unit between the lower gum and the oral mucosa opposite thereto of the individual undergoing drug therapy. Excipients or vehicles suitable for buccal drug administration can be used, and include any such materials known in the art, e.g., any liquid, gel, solvent, liquid diluent, solubilizer, or the like, which is nontoxic and does not interact with other components of the composition in a deleterious manner. A solid dosage unit is fabricated so as to dissolve gradually over a predetermined time period, to produce a substantially saturated drug solution in the saliva of the buccal cavity, allowing absorption of cladribine through the mucosa, wherein drug delivery is provided essentially throughout the time period. The buccal dosage unit may further comprise a lubricant to facilitate manufacture, e.g., magnesium stearate or the like. Additional components that may be included in the buccal dosage unit include but are not limited to flavorings, permeation enhancers, diluents, binders, and the like. The remainder of the buccal dosage unit may comprise a bioerodible polymeric carrier, and any excipients that may be desired, e.g., binders, disintegrants, lubricants, diluents, flavorings, colorings, and the like, and/or additional active agents.

The buccal carrier can comprise a polymer having sufficient tack to ensure that the dosage unit adheres to the buccal mucosa for the necessary time period, i.e., the time period during which the cladribine is to be delivered to the buccal mucosa. Additionally, the polymeric carrier is gradually "bioerodible", i.e., the polymer hydrolyzes at a predetermined rate upon contact with moisture. Any polymeric carriers can be used that are pharmaceutically acceptable, provide both a suitable degree of adhesion and the desired drug release profile, and are compatible with the cladribine to be administered and any other components that may be present in the buccal dosage unit. Generally, the polymeric carriers comprise hydrophilic (water-soluble and water-swellable) polymers that adhere to the wet surface of the buccal mucosa. Examples of polymeric carriers useful herein include acrylic acid polymers and copolymers, e.g., those known as "carbomers" for example, Carbopol®. Other suitable polymers include, but are not limited to, hydrolyzed polyvinyl alcohol, polyethylene oxides (e.g., Sentry Polyox®), polyacrylates (e.g., Gantrez®), vinyl polymers and copolymers, polyvinylpyrrolidone, dextran, guar gum, pectins, starches, and cellulosic polymers such as hydroxypropyl methylcellulose (e.g., Methocel®), hydroxypropyl cellulose (e.g., Klucel®), hydroxypropyl cellulose ethers, hydroxyethyl cellulose, sodium carboxymethyl cellulose, methyl cellulose, ethyl cellulose, cellulose acetate phthalate, cellulose acetate butyrate, and the like. The dosage unit need contain only the saturated cladribine-cyclodextrin complex. However, it may be desirable in some cases to include one or more of the aforenoted carriers and/or one or more additional components. For example, a lubricant may be included to facilitate the process of manufacturing the dosage units; lubricants may also optimize erosion rate and drug flux. If a lubricant is present, it will represent on the order of 0.01 wt. % to about 2 wt. %, preferably about 0.01 wt. % to 1.0 wt. %, of the dosage unit. Suitable lubricants include, but are not limited to, magnesium stearate, calcium stearate, stearic acid, sodium stearylfumarate, talc, hydrogenated vegetable oils and polyethylene glycol.

The saturated cladribine-cyclodextrin complex may also be administered in accord with this invention in the form of suppositories or foams for vaginal or rectal administration. These compositions can be prepared by well-known methods, for example, in the case of suppositories, by mixing the saturated complex with a suitable non-irritating excipient or binder which is solid at ordinary temperatures but liquid at the vaginal or rectal temperature and will, therefore, melt in the vagina or rectum to release the drug. Such materials include cocoa butter and polyethylene glycols. Traditional binders and carriers include, for example, polyalkylene glycols or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

For intranasal use, a powder spray, gel or ointment may be utilized, preferably a powder form of the saturated complex.

Moreover, for use in humans, a buccal dosage form, especially a buccal tablet or wafer or disk, advantageously having a disintegration time of about 15-30 minutes, or a buccal patch (in which the drug is released only from the side which adheres to the buccal mucosa while the other side is nonpermeable), is of interest. Buccal administration may make use of the inventions of Nagai et al. described in U.S. Pat. Nos. 4,226,848 and 4,250,163, both of which are incorporated by reference herein in their entireties and relied upon. Thus, a buccal mucosa-adhesive tablet may be formulated for use herein comprising: (a) a water-swellable and mucosa-adhesive polymeric matrix comprising about 50% to about 95% by weight of a cellulose ether and about 50% to about 95% by weight of a homo- or copolymer of acrylic acid or a pharmaceutically acceptable salt thereof, and (b) dispersed therein, an appropriate quantity of cladribine, as a saturated complex with 2-hydroxypropyl-β-cyclodextrin or γ-cyclodextrin. Ideally, for storage stability, the tablet is anhydrous.

The methods and pharmaceutical compositions described herein offer novel therapeutic modalities for the treatment of patients in need of treatment with cladribine. As shown herein, the invention addresses the problems of poor bioavailability traditionally associated with oral cladribine. Alternatively, the orogastric route may be avoided entirely by administering a transmucosal delivery form.

The compositions of the invention are particularly suitable as modalities for the treatment of any cladribine-responsive disease. Several disease states responsive to cladribine are well-documented in the literature (see infra). For any target disease state, an effective amount of the optimized cladribine-cyclodextrin complex is used (e.g., an amount effective for the treatment of multiple sclerosis, rheumatoid arthritis, or leukemia).

The term "therapeutically effective amount" or "effective amount" is used to denote treatments at dosages effective to achieve the therapeutic result sought. Therapeutically effective dosages described in the literature include those for hairy cell leukemia (0.09 mg/kg/day for 7 days), for multiple sclerosis (from about 0.04 to about 1.0 mg/kg/day (see U.S. Pat. No. 5,506,214)); for other diseases, see also U.S. Pat. Nos. 5,106,837 (autohemolytic anemia); 5,310,732 (inflammatory bowel disease); 5,401,724 (rheumatoid arthritis); 5,424,296 (malignant astrocytoma); 5,510,336 (histiocytosis); 5,401,724 (chronic myelogenous leukemia); and 6,239,118 (atherosclerosis).

Further, various dosage amounts and dosing regimens have been reported in the literature for use in the treatment of multiple sclerosis; see, for example: Romine et al., *Proceedings of the Association of American Physicians*, Vol. 111, No. 1, 35-44 (1999); Selby et al., *The Canadian Journal of Neurological Sciences*, 25, 295-299 (1998); Tortorella et al., *Current Opinion in Investigational Drugs*, 2 (12), 1751-1756 (2001); Rice et al., *Neurology*, 54, 1145-1155 (2000); and Karlsson et al., *British Journal of Haematology*, 116, 538-548 (2002); all of which are incorporated by reference herein in their entireties and relied upon.

Moreover, the route of administration for which the therapeutically effective dosages are taught in the literature should be taken into consideration. While the instant compositions optimize the bioavailability of cladribine following oral or transmucosal administration, it will be appreciated that even optimal bioavailability from oral or transmucosal dosage forms is not expected to approach bioavailability obtained after intravenous administration, particularly at early time points; see, for example, FIG. 3 hereinafter. Thus, it is often appropriate to increase a dosage suggested for intravenous administration to arrive at a suitable dosage for incorporation into a solid oral dosage form or a transmucosal dosage form. At the present time, it is envisioned that, for the treatment of multiple sclerosis, 10 mg of cladribine in the instant solid dosage form as the saturated cladribine-cyclodextrin complex would be administered once per day for a period of five to seven days in the first month, repeated for another period of five to seven days in the second month, followed by ten months of no treatment. Alternatively, the patient would be administered the 10 mg dose once per day for a period of five to seven days per month for six months, followed by eighteen months of no treatment.

Furthermore, one of skill will appreciate that the therapeutically effective amount of cladribine administered herein may be lowered or increased by fine tuning and/or by administering cladribine according to the invention with another active ingredient. The invention therefore provides a method to tailor the administration/treatment to the particular exigencies specific to a given mammal. Therapeutically effective amounts may be easily determined, for example, empirically by starting at relatively low amounts and by step-wise increments with concurrent evaluation of beneficial effect.

As noted in the preceding paragraph, administration of cladribine in accord with this invention may be accompanied by administration of one or more additional active ingredients for treating the cladribine-responsive condition. The additional active ingredient will be administered by a route of administration and in dosing amounts and frequencies appropriate for each additional active ingredient and the condition being treated. For example, in the treatment of multiple sclerosis, other useful drugs include interferon beta (Rebif®, Betaseron®/Betaferon®, Avonex®), identical to the naturally occurring protein found in the human body; glatiramer acetate (Copaxone®), a random chain (polymer) of the amino acids glutamic acid, lysine, alanine and tyrosine; natalizumab (Antegren®), a monoclonal antibody; alemtuzumab (Campath-1H®), a humanized anti-CD52 monoclonal antibody; 4-aminopyridine (also known as 4-AP and Fampridine), a drug that blocks the potassium channels in neurons; and amantadine, an anti-viral agent which improves muscle control and reduces muscle stiffness and is used to alleviate the symptoms of fatigue in multiple sclerosis, a purpose for which pemoline (Cylert®) and L-Carnitine (a herbal product) may also be useful. In the treatment of hairy cell leukemia, additional active ingredients may include interferon alpha, pentostatin, fludarabine, rituximab (an anti-CD 20 monoclonal antibody) and the anti-CD22 recombinant immunotoxin BL 22; other additional active ingredients may be appropriate in other types of leukemias. In the treatment of rheumatoid arthritis, there are many other active ingredients which may be selected. These include NSAIDS (non-steroidal anti-inflammatory drugs), which are of three types: salicylates such as aspirin, traditional NSAIDS such as ibuprofen and indomethacin, and COX-2 inhibitors such as celecoxib (Celebrex®), rofecoxib (Vioxx®), meloxicam (Mobic®), valdecoxib (Bextra®), lumiracoxib (Prexige®) and etoricoxib (Arcoxia®). Other drugs useful in treating rheumatoid arthritis which may be used in conjunction with the present invention include DMARDS, glucocorticoids, biological response modifiers and non-NSAID analgesics. DMARDS are disease-modifying anti-rheumatic drugs which include methotrexate, plaquenil, leflunomide (Arava®), sulfasalazine, gold, penicillamide, cyclosporine, methyl cyclophosamide and azathioprine. Glucocorticoids include dexamethasone, prednisolone, triamcinolone and many others. Biological response modifiers (which restore the disease-fighting ability of the immune system), include etanercept (Enrel®), a tumor-necrosis factor inhibitor, infliximab (Remicade®), which is also an anti-TNF drug, anakinra (Kineret®), a selective IL-1 blocker, and Humira®, a human monoclonal antibody which is another anti-TNF drug. The non-NSAID analgesics include acetaminophen as well as narcotic analgesics such as hydrocodone, oxycodone and propoxyphene. Generally speaking, those drugs which work by a mechanism different from that of cladribine are particularly useful for concomitant therapy with the cladribine composition described herein. Those drugs which are effective by the oral or transmucosal route of administration and which are compatible with the instant cladribine complexes in a single dosage form may be incorporated into the instant dosage forms; otherwise, they should of course be separately administered in amounts, frequencies and via administration routes suitable to them.

As used herein, "treating" means reducing, preventing, hindering the development of, controlling, alleviating and/or reversing the symptoms in the individual to which a compound of the invention has been administered, as compared to the symptoms of an individual not being treated according to the invention. A practitioner will appreciate that the complexes, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The methods of the present invention are intended for use with any subject/patient that may experience the benefits of the methods of the invention. Thus, in accordance with the invention, the terms "subjects" as well as "patients" include humans as well as non-human subjects, particularly domesticated animals.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Phase Solubility Study

A phase solubility study was carried out as follows. Excess cladribine was added to cyclodextrin solutions of various concentrations of γ-cyclodextrin (γCD) or hydroxypropyl-β-cyclodextrin (HPβCD) and allowed to complex as described in Example 2 below. In addition, in one set of experiments, the effect of hydroxypropylmethyl cellulose (HPMC) on complexation was investigated. The excess, undissolved cladribine was removed by filtration. The amount of cladribine in the complexation solution was measured to obtain a data point. This process was repeated with different known concentrations of cyclodextrin until several data points were obtained. These data points were then plotted graphically, each data point representing the maximum amount of cladribine that can be complexed with a specific concentration of cyclodextrin, i.e. each point represents a saturated cladribine-cyclodextrin complex. Points on the line generated by the data points represent HTA ratios. Any point on the line represents a specific, unique saturated cladribine-cyclodextrin complex. One of skill in the art will realize the same results will be generated if excess cyclodextrin is added to cladribine solutions of known concentration.

As an example, cyclodextrin solutions of varying concentrations were prepared and saturated with cladribine by providing cladribine in excess. Saturated cyclodextrin solutions for a given cyclodextrin at a given cyclodextrin concentration are exemplified in Table I below.

TABLE I

| Cyclodextrin | Cladribine-HPβCD (Trial A) | | | Cladribine-HPβCD and HPMC (0.1%) (Trial B) | | | Cladribine-γCD (Trial C) | | |
|---|---|---|---|---|---|---|---|---|---|
| Molar Conc. | Absorbance | mg/ml | Molar conc. | Absorbance | mg/ml | Molar conc. | Absorbance | mg/ml | Molar conc. |
| 0.00 | 0.140 | 2.610 | 0.0091 | 0.137 | 2.550 | 0.0089 | 0.132 | 2.459 | 0.0086 |
| 0.018 | 0.169 | 3.139 | 0.011 | 0.146 | 2.711 | 0.0095 | 0.1352 | 2.519 | 0.0088 |
| 0.035 | 0.191 | 3.554 | 0.0124 | 0.175 | 3.262 | 0.0114 | 0.1531 | 2.852 | 0.0100 |
| 0.071 | 0.245 | 4.570 | 0.016 | 0.223 | 4.149 | 0.0145 | 0.1542 | 2.873 | 0.0101 |
| 0.142 | 0.333 | 6.211 | 0.0217 | 0.332 | 6.185 | 0.0216 | 0.1965 | 3.661 | 0.0128 |
| 0.285 | 0.514 | 9.581 | 0.0335 | 0.259 | 4.831 | 0.0169 | 0.4688 | 8.733 | 0.0306 |

The molar concentrations of cladribine to cyclodextrin in Table I are plotted and presented graphically as FIG. 1. The plotted lines for cladribine-HPβCD, cladribine-HPβCD and 0.1% HPMC, and cladribine-γCD represent maximal cladribine solubilization for the conditions tested, that is, the HTA ratio of the concentration of cladribine to the concentration of cyclodextrin. The area above each of the plotted lines represents conditions where excess insoluble cladribine is present. The area below each of the plotted lines represents the conditions where cyclodextrin is in excess of the amount needed to maintain the complex in solution. Clearly, the data in Table I and in FIG. 1 shows that HPMC, a known complexation facilitator, has no effect at lower concentrations and has a negative effect at higher concentrations.

The HTA plot for cladribine-HPβCD shown in FIG. 1 is approximately linear; this is indicative of a 1:1 complex, in which one molecule of the drug is complexed with one molecule of cyclodextrin. FIG. 1 also shows that additional cyclodextrin is needed to maintain the cladribine in the complex. For example, in the case of γ-cyclodextrin, about 0.10 mole of γCD is needed to maintain about 0.01 mole of cladribine in its saturated complex; in the case of HPβCD, about 0.10 mole of cyclodextrin is needed to maintain about 0.017 mole of cladribine in its saturated complex. However, in the case of γCD, drug solubility significantly increases at higher concentrations of the cyclodextrin; at a molar concentration of γCD of about 0.15, the slope of the line changes, indicating formation of a 1:2 complex of cladribine to cyclodextrin, that is, one molecule of cladribine is complexed with 2 molecules of γ-CD, which essentially surround and protect the cladribine molecule.

The two molecules of γ-CD are believed to hydrogen-bond to each other at high cyclodextrin concentration and incorporate in the cavity between them the cladribine molecule. This is thought to be a stepwise process, in which the 1:1 complex first forms, then a second γ-CD molecule H-bonds with the γ-CD in the 1:1 complex, forming the 1:2 complex. Of course, frequently a mixture of 1:1 and 1:2 complexes will be obtained, but a predominance of the 1:2 complex is advantageous. Thus, in the case of γ-CD, a molar concentration of about 0.20 of the cyclodextrin maintains about 0.017 mole of cladribine in its saturated complex. At higher cyclodextrin and drug concentrations, then, there is less difference between γCD and HPβCD in the amount of cyclodextrin needed for a given amount of cladribine, and γ-CD dissolves proportionately more cladribine than does HPβCD. Since the 1:2 complex formed at higher concentrations of γCD is a stronger complex than a 1:1 complex, the cladribine in the saturated solution formed when such a 1:2 complex releases the drug in the body fluid at the mucosa is even more unstable, i.e. has even higher thermodynamic activity, than the cladribine released from a 1:1 complex, favoring even greater movement of the drug through the mucosa. The complex with γCD is also advantageous because γCD is a natural cyclodextrin, thus presents fewer issues vis-à-vis toxicity. Further, in the case of solid oral dosage forms, it is believed that the 1:2 complex with γ-CD will better protect the cladribine from attack by stomach acid because it is able to essentially surround the drug molecule with cyclodextrin and thus is uniquely well-suited for the purposes of this invention.

Example 2

Preparation of Cladribine-Cyclodextrin Complex

Part A:

Cladribine is complexed with either HPβCD or γCD by the following general method.

An aqueous suspension of cladribine, in excess, and a concentrated solution (approximately 27% for γ-cyclodextrin and approximately 40% for HPβCD) of cyclodextrin are mixed with stirring at room temperature for about nine hours. This achieves equilibration. Excess, non-complexed cladribine, if any, is removed by filtration. To form the solid saturated cladribine-cyclodextrin complex, the aqueous cladribine-cyclodextrin solutions are dried by lyophilization prior to incorporation into solid buccal or oral tablets. The lyophilization procedure comprises a freezing stage of rapidly bringing the complexation solution to a temperature of from about −40° C. to about −80° C. for a period of from about 2 to 4 hours, preferably from about 3 to 4 hours, for example a temperature of about −45° C. for approximately 200 minutes, followed by a primary drying stage at about −25° C. for approximately 80-90 hours, typically under low pressure, and then a secondary drying stage at about 30° C. for about 15-20 hours.

Product made by the foregoing general procedure can be analyzed by HPLC (utilizing a Hypersil ODS 3 micron column and an acetonitrile based mobile phase, with UV detection at 264 nm) to find the weight ratio of cladribine to cyclodextrin in the final product. Final product preparations can be further characterized by methods known in the art, including, for example by inspecting appearance, ascertaining the overall impurity content by HPLC, ascertaining the water content using a Karl Fischer titrator, determining the dissolution profile by a standard method, for example using U.S. Pat. No. <711> Apparatus II equipment and UV detection at 264 nm, inspecting the content uniformity and performing quantitative assay by HPLC analysis of the active ingredient.

Part B:

Two batches of cladribine/cyclodextrin product, FD02, in which γ-CD was used, and FD03 in which HPβCD was used, were prepared by the foregoing general procedure as follows:

Purified water (585 ml for FD02 and 575 ml for FD03) was dispensed into a 1 liter glass vessel for each batch. The γ-cyclodextrin (116 g) and 2-hydroxypropyl-β-cyclodextrin (115 g) were weighed and slowly added to the stirred water over a period of 30 minutes. Cladribine (2.53 g for FD02 and 2.76 g for FD03) was weighed and added to the respective stirred cyclodextrin solutions. The solutions were sonicated for 20 minutes. The resulting clear solution was stirred at room temperature for 9 hours. The solutions were then filled into 100 ml lyophilization vials (20 ml solution per vial) and the filled vials were partially stoppered. The lyophilization included freezing at −45° C. for about 3.3 hours, a primary drying phase at −25° C. under a pressure of 100 mTorr for about 85.8 hours, and a secondary drying phase at 30° C. for about 17.5 hours as set forth below:

| | LYOPHILIZATION CYCLE | | | |
|---|---|---|---|---|
| Step | Process | Temperature | Pressure (mTorr) | Time (hrs) |
| 1 | Load | 4° C. | | |
| 2 | Load Hold | 4° C. | n/a | 2.0 |
| 3 | Ramp | −45° C. | n/a | 2.0 |
| 4 | Freezing | −45° C. | n/a | 3.3 |
| 5 | Ramp | −25° C. | 100 | 2.2 |
| 6 | Primary drying | −25° C. | 100 | 85.8 |
| 7 | Ramp | 30° C. | 50 | 4.0 |
| 8 | Secondary drying | 30° C. | 50 | 17.5 |
| 9 | Finish | 30° C. | Vials closed under vacuum | |

The FD02 and FD03 batches of cladribine/cyclodextrin made by the foregoing procedure were analyzed by HPLC (utilizing a Hypersil ODS 3 micron column and an acetonitrile based mobile phase with UV detection at 264 nm) and empirically found to have the following characteristics:

| Complex | Weight:Weight | Weight Ratio |
|---|---|---|
| Cladribine: γ-CD | 2.53 g:116.0 g | 1:46 |
| Cladribine: HPβCD | 2.76 g:115.0 g | 1:42 |

The products were analyzed by DSR and X-ray diffraction methods to determine any free cladribine in the lyophilized material. Importantly, the samples exhibited no transitions in the region of 210° C. to 230° C., which is associated with the melting of crystalline cladribine. In both cases, no significant thermal activity was recorded in the range of 210° C. to 230° C., suggesting that the complexes obtained at the end of the lyophilization do not have any significant amount of free crystalline cladribine, considering the sensitivity of the analytical method (up to 3% w/w). This conclusion was supported by the absence of peaks for crystalline cladribine from X-ray diffraction traces for both complexes FD02 and FD03.

As noted above, these cladribine:cyclodextrin complexes have cladribine:cyclodextrin weight ratios of about 1:46 for cladribine: γ-cyclodextrin and about 1:42 for cladribine:hydroxypropyl-β-cyclodextrin. Cladribine:cyclodextrin weight ratios close to these, for example from about 1:35 to about 1:50, are most desirable. These ratios can vary depending upon the particular cyclodextrin used and the amount of cyclodextrin in the complexation solution, as well as the complexation temperature.

Example 3

Pharmacokinetic Studies

The bioavailability of cladribine when complexed with γCD or HPβCD was evaluated in a beagle dog model. The data obtained from this model are expected to be representative for the human experience.

The saturated cladribine-cyclodextrin complex as prepared in EXAMPLE 2, Part B, FD02 and FD03, were used to prepare oral and buccal tablets. The complex materials were passed through a #18 mesh (0.9 mm) screen with magnesium stearate, blended for five minutes and compressed using 10 mm punches. The 10 mm tablets had upper shallow convex tooling and lower flat beveled edge tooling. The formulations for the manufacture were as follows:

TABLE II

PART A

| Batch No. | | RDT-0418/C | RDT-0418/D |
|---|---|---|---|
| Ingredient | Lot Number | mg/tablet | mg/tablet |
| Cladribine/γ-CD complex | FD 02 | 232.65* | |
| Cladribine/2-HPβCD complex | FD 03 | | 212.85* |
| Magnesium stearate | | 2.35 | 2.15 |
| Total | | 235.00 | 215.00 |

*This amount of complex contains approximately 5 mg of cladribine/tablet.

TABLE II

PART B

| Property of Finished Tablet | Cladribine: γ-Cyclodextrin Tablet RDT-0418/C | Cladribine: HP-β-Cyclodextrin Tablet RDT-0418/D |
|---|---|---|
| Average Weight | 237.0 mg | 217 mg |
| Hardness | 4.0 Kp | 3.72 Kp |
| Friability | 0.5% | 0.4% |
| Thickness | 3.8 mm | 3.3 mm |
| Disintegration | 8 minutes | 8 minutes |

Bioavailability and pharmacokinetic studies were conducted in a beagle dog model as follows.

Outbred male beagle dogs (identified as PM01-PM06) obtained from IDRI (Dunakeszi, Hungary) were allowed laboratory diet and water ad libitum. The same dogs were used throughout the study to minimize inter- and intrasubject variability. The bioavailability and pharmacokinetic studies were conducted as follows.

In the first test period, 5 mg cladribine (0.25 mg/ml in isotonic saline) was administered intravenously to test subjects. Blood samples were collected at various time intervals over 48 hours. In the second test period, half of the subjects received buccally a tablet as described above containing a saturated cladribine-γCD or -HPβCD complex. Serial blood samples were collected over 48 hours. The third test period repeated the second test period with the exception that the subjects previously receiving the γ-cyclodextrin buccal tablet were now given hydroxypropyl-β-cyclodextrin buccal tablets, with hydroxypropyl-β-cyclodextrin tablet recipients from the second period receiving γ-cyclodextrin buccal tablets. The fourth and fifth test periods repeated test periods two and three with the exception that the tablets were given orally.

Cladribine levels in the blood were measured by HPLC and an LC/MS/MS method. The TopFit 2.0 Pharmacokinetic and Pharmacodynamic Data Analysis System was used for the pharmacokinetic analysis of the data. The results of the bioavailability study for control (intravenous) and cladribine-cyclodextrin complexes are presented in Tables III to VII and summarized in Table VIII.

The headings of the columns in Table III are defined as follows:

$C_{initial}$ is the extrapolated value at the end of the bolus;
$C_{first}$ is the first measured concentration at 5 minutes after the dose is administered;
t½ terminal is the terminal elimination half-life;
AUD is the area under the measured data, integrated with the linear trapezoidal rule;
$AUD_{ext}$ is the extrapolated area from the last measured time-point to infinity;
AUC is AUD extrapolated to infinity;
$Cl_{tot}$ is total clearance (dose/AUC); and
$MRT_{tot}$ is the mean residence time.

The headings of the columns in Tables IV to VII are defined as follows:

$C_{max}$ is the peak concentration measured;
$T_{max}$ is the time to $C_{max}$;
t½ terminal is the terminal elimination half-life;
AUD is the area under the measured data, integrated with the linear trapezoidal rule;
$AUD_{ext}$ is the extrapolated area from the last measured time-point to infinity;
AUC is AUD extrapolated to infinity;
$MRT_{tot}$ is the mean residence time; and
F is the bioavailability expressed in %.

The peak areas, calibration curves, accuracy, precision values and the concentrations were determined using Analyst Software 1.1 (PE SCIEX, Foster City, US). For calculation of mean and standard deviation, Excel 5.0 software was used. The calibration curve was fitted using the ratio of concentrations of analyte and internal standard versus the ratio of the peak areas of them. A straight line was fitted on the experimental points by weighted least squares linear regression analysis. The weighting scheme used was 1/concentration squared as pg/ml plasma.

At early time-points after intravenous administration, the plasma concentrations exceeded the upper limit of the calibration curve. Thus a lower amount of the sample was re-injected to prove the linear detector response. Since the standard/internal standard ratio remained the same at the appropriate detector response, concentrations higher than 100 ng/ml could be accepted. For calculation of mean, standard deviation and CV %, Excel 5.0 software was used. Lower levels than the limit of quantification were not accepted. Mean and S.D. values were calculated only for the concentrations measured after intravenous administration.

TABLE III

Intravenous bolus, 5 mg cladribine/animal

| Dog | $C_{initial}$ (ng/ml) | $C_{first}$ (ng/ml) | t½ terminal (h) | AUD (ng · h/ml) | $AUD_{ext}$ (%) | AUC (ng · h/ml) | $Cl_{tot}$ (ml/min) | $MRT_{tot}$ (h) | Body Weight (kg) | Dose (mg/kg) | AUC/ Dose | $Cl_{tot}$/kg (ml/min/kg) |
|---|---|---|---|---|---|---|---|---|---|---|---|---|
| PM01 | 655 | 560 | 10.4 | 426 | 1.4 | 432 | 193 | 1.3 | 10.98 | 0.46 | 949 | 17.6 |
| PM02 | 525 | 446 | 8.5 | 337 | 1.4 | 342 | 244 | 1.2 | 13.86 | 0.36 | 948 | 17.6 |
| PM03 | 726 | 605 | 10.7 | 426 | 1.5 | 433 | 192 | 1.3 | 12.44 | 0.40 | 1077 | 15.4 |
| PM04 | 569 | 477 | 11.0 | 379 | 1.4 | 383 | 217 | 1.4 | 11.98 | 0.42 | 918 | 18.1 |
| PM05 | 335 | 306 | 11.3 | 334 | 1.0 | 338 | 247 | 1.5 | 14.28 | 0.35 | 965 | 17.3 |
| PM06 | 567 | 478 | 9.9 | 359 | 1.9 | 366 | 228 | 1.3 | 12.94 | 0.39 | 947 | 17.6 |
| Mean | 563 | 479 | 10.3 | 377 | 1.4 | 382 | 220 | 1.3 | 12.75 | 0.40 | 967 | 17.3 |
| S.D. | 133 | 103 | 1.0 | 41 | 0.3 | 42 | 24 | 0.1 | 1.22 | 0.04 | 56 | 0.9 |
| CV % | 24 | 22 | 9.8 | 11 | 20 | 11 | 11 | 9 | 10 | 10 | 6 | 5 |

TABLE IV

Buccal administration 5 mg cladribine/animal
Tablet-1: γ-cyclodextrin complex (RDT-0418/C)

| Dog | $C_{max}$ (ng/ml) | $T_{max}$ (h) | t½ terminal (h) | AUD (ng · h/ml) | $AUD_{ext}$ (%) | AUC (ng · h/ml) | $MRT_{tot}$ (h) | Body Weight (kg) | Dose (mg/kg) | AUC/ Dose | F (%) |
|---|---|---|---|---|---|---|---|---|---|---|---|
| PM01 | 31.1 | 4.0 | 15.1 | 115 | 1.8 | 117 | 6.7 | 12.16 | 0.41 | 285 | 30.0 |
| PM02 | 78.8 | 2.0 | 16.9 | 159 | 1.2 | 161 | 4.2 | 14.72 | 0.34 | 474 | 50.0 |
| PM03 | 107.0 | 2.0 | 21.5 | 214 | 1.6 | 218 | 4.6 | 12.50 | 0.40 | 545 | 50.6 |
| PM04 | 37.3 | 1.5 | 13.3 | 96 | 1.0 | 97 | 4.2 | 13.02 | 0.38 | 253 | 27.5 |
| PM05 | 30.7 | 3.0 | 9.2 | 92 | 0.4 | 93 | 4.9 | 15.52 | 0.32 | 289 | 29.9 |
| PM06 | 65.4 | 3.0 | 13.2 | 108 | 0.7 | 109 | 4.5 | 14.40 | 0.35 | 314 | 33.1 |
| Mean | 58.4 | 2.6 | 14.9 | 131 | 1.1 | 133 | 4.8 | 13.72 | 0.37 | 360 | 36.9 |
| S.D. | 30.9 | 0.9 | 4.1 | 47 | 0.5 | 48 | 1.0 | 1.35 | 0.04 | 120 | 10.6 |
| CV % | 53 | 36 | 28 | 36 | 48 | 37 | 20 | 10 | 10 | 33 | 29 |

TABLE V

Buccal administration; 5 mg cladribine/animal
Tablet-2: hydroxypropyl-β-cyclodextrin complex (RDT-0418/D)

| Dog | $C_{max}$ (ng/ml) | $T_{max}$ (h) | t½ terminal (h) | AUD (ng·h/ml) | $AUD_{ext}$ (%) | AUC (ng·h/ml) | $MRT_{tot}$ (h) | Body Weight (kg) | Dose (mg/kg) | AUC/Dose | F (%) |
|---|---|---|---|---|---|---|---|---|---|---|---|
| PM01 | 78.0 | 2.0 | 10.9 | 128 | 0.5 | 129 | 3.7 | 12.32 | 0.41 | 318 | 33.5 |
| PM02 | 95.6 | 0.8 | 13.8 | 102 | 1.3 | 103 | 3.7 | 14.96 | 0.33 | 308 | 32.5 |
| PM03 | 54.0 | 2.0 | 9.1 | 106 | 0.6 | 107 | 4.7 | 12.90 | 0.39 | 276 | 25.6 |
| PM04 | 51.5 | 1.0 | 15.5 | 120 | 0.8 | 121 | 3.3 | 12.74 | 0.39 | 308 | 33.6 |
| PM05 | 50.9* | 0.75* | 13.9 | 83* | 0.6* | 84* | 2.88* | 15.08 | 0.33 | 253* | 29.6* |
| PM06 | 33.4 | 2.0 | 13.1 | 84 | 1.4 | 85 | 5.3 | 13.68 | 0.37 | 233 | 24.6 |
| Mean | 62.5 | 1.6 | 12.7 | 108 | 0.9 | 109 | 4.1 | 13.61 | 0.37 | 289 | 30.0 |
| S.D. | 24.4 | 0.6 | 2.3 | 17 | 0.4 | 17 | 0.8 | 1.18 | 0.03 | 35 | 4.5 |
| CV % | 39 | 40 | 18 | 16 | 44 | 16 | 20 | 9 | 8 | 12 | 15 |

*excluded from mean (because the subject swallowed the drug form)

TABLE VI

Oral administration; 5 mg cladribine/animal
Tablet-1: γ-cyclodextrin complex (RDT-0418/C)

| Dog | $C_{max}$ (ng/ml) | $T_{max}$ (h) | t½ terminal (h) | AUD (ng·h/ml) | $AUD_{ext}$ (%) | AUC (ng·h/ml) | $MRT_{tot}$ (h) | Body Weight (kg) | Dose (mg/kg) | AUC/Dose | F (%) |
|---|---|---|---|---|---|---|---|---|---|---|---|
| PM01 | 218.9 | 0.8 | 11.0 | 193 | 0.4 | 194 | 2.6 | 12.70 | 0.39 | 493 | 51.9 |
| PM02 | 141.2 | 0.5 | 10.2 | 156 | 0.3 | 156 | 2.3 | 15.08 | 0.33 | 470 | 49.6 |
| PM03 | 234.9 | 0.3 | 13.3 | 214 | 0.4 | 215 | 1.9 | 13.18 | 0.38 | 567 | 52.6 |
| PM04 | 99.6 | 2.0 | 16.2 | 172 | 0.8 | 174 | 3.5 | 13.18 | 0.38 | 459 | 50.0 |
| PM05 | 17.6* | 1.5* | 10.2* | 52* | 2* | 53* | 3.29* | 15.52 | 0.32 | 165* | 17.0* |
| PM06 | 161.8 | 0.3 | 11.1 | 148 | 0.4 | 148 | 2.1 | 14.52 | 0.34 | 430 | 45.4 |
| Mean | 171.3 | 0.8 | 12.4 | 177 | 0.5 | 177 | 2.5 | 14.03 | 0.36 | 484 | 49.9 |
| S.D. | 55.8 | 0.7 | 2.4 | 27 | 0.2 | 27 | 0.6 | 1.16 | 0.03 | 52 | 2.8 |
| CV % | 33 | 97 | 20 | 15 | 42 | 15 | 25 | 8 | 8 | 11 | 6 |

*excluded from mean (because the values obtained were highly anomalous compared to those for other subjects)

TABLE VII

Oral administration; 5 mg cladribine/animal
Tablet-2: hydroxypropyl-β-cyclodextrin complex (RDT-0418/D)

| Dog | $C_{max}$ (ng/ml) | $T_{max}$ (h) | t½ terminal (h) | AUD (ng·h/ml) | $AUD_{ext}$ (%) | AUC (ng·h/ml) | $MRT_{tot}$ (h) | Body Weight (kg) | Dose (mg/kg) | AUC/Dose | F (%) |
|---|---|---|---|---|---|---|---|---|---|---|---|
| PM01 | 143.3 | 0.5 | 12.8 | 174 | 0.5 | 175 | 2.3 | 12.72 | 0.39 | 445 | 46.9 |
| PM02 | 86.9 | 1.5 | 10.6 | 121 | 0.5 | 122 | 3.4 | 15.00 | 0.33 | 366 | 38.6 |
| PM03 | 231.5 | 0.3 | 12.6 | 199 | 0.4 | 200 | 2.0 | 13.24 | 0.38 | 530 | 49.2 |
| PM04 | 114.3 | 1.5 | 15.0 | 171 | 0.8 | 172 | 3.7 | 13.16 | 0.38 | 453 | 49.3 |
| PM05 | 147.5 | 1.0 | 14.2 | 149 | 0.7 | 150 | 3.2 | 15.32 | 0.33 | 460 | 47.6 |
| PM06 | 68.5 | 0.5 | 16.9 | 121 | 0.9 | 123 | 2.8 | 14.32 | 0.35 | 352 | 37.2 |
| Mean | 132.0 | 0.9 | 13.7 | 156 | 0.6 | 157 | 2.9 | 13.96 | 0.36 | 434 | 44.8 |
| S.D. | 57.7 | 0.5 | 2.2 | 31 | 0.2 | 31 | 0.6 | 1.07 | 0.03 | 66 | 5.4 |
| CV % | 44 | 62 | 16 | 20 | 31 | 20 | 22 | 8 | 8 | 15 | 12 |

TABLE VIII

Bioavailability of cladribine in dogs
(dose given in mg cladribine/animal)

| | γ-Cyclodextrin Complex | | | HP-β-Cyclodextrin Complex | | |
|---|---|---|---|---|---|---|
| Dog | Buccal (5 mg) | Oral (5 mg) | Oral[a] (5 mg) | Buccal (5 mg) | Oral (5 mg) | Oral[a] (5 mg) |
| PM01 | 30.0 | 51.9 | 35.3 | 33.5 | 46.9 | 17.0 |
| PM02 | 50.0 | 49.6 | 39.5 | 32.5 | 38.6 | 19.0 |
| PM03 | 50.6 | 52.6 | 27.4 | 25.6 | 49.2 | 25.1 |
| PM04 | 27.5 | 50.0 | 24.9 | 33.6 | 49.3 | 26.5 |

TABLE VIII-continued

Bioavailability of cladribine in dogs
(dose given in mg cladribine/animal)

| | γ-Cyclodextrin Complex | | | HP-β-Cyclodextrin Complex | | |
|---|---|---|---|---|---|---|
| Dog | Buccal (5 mg) | Oral (5 mg) | Oral[a] (5 mg) | Buccal (5 mg) | Oral (5 mg) | Oral[a] (5 mg) |
| PM05 | 29.9 | 17.0* | 36.1 | 29.6** | 47.6 | 27.1 |
| PM06 | 33.1 | 45.4 | 42.3 | 24.6 | 37.2 | 31.7 |
| Mean | 36.9 | 49.9 | 34.2 | 30.0 | 44.8 | 24.5 |
| S.D. | 10.6 | 2.8 | 6.8 | 4.5 | 5.4 | 5.3 |
| CV % | 29 | 6 | 20 | 15 | 12 | 21 |

*excluded from mean (because the values obtained were highly anomalous compared to those for the other subjects)
**excluded from mean (because the subject swallowed the drug form)
[a] excess cyclodextrin, ≈10x that for the saturated complex. The total amount of cyclodextrin in these studies is ~2.5 gm with 5 mg cladribine.

Pharmacokinetic analysis was performed on the basis of individual plasma concentration versus time curves. The mean and S.D. of parameters obtained from individual data were calculated. The linear-trapezoidal rule was used for calculation of the area under the plasma concentration time curve from 0 until the last measured concentration (AUD). Using the terminal regression line the area extrapolated to infinity ($AUC_{t-\infty}$) was calculated in the following way: $AUC_{t-\infty} = c_{calc}/\lambda_z$ where: $C_{calc}$ represents the estimated plasma concentration by the regression line at the last sampling time point with measured concentration above the limit of quantification, and $\lambda_z$ represents the rate constant calculated from the regression line.

The points determining the regression line, i.e. the terminal phase, were selected by visual determination of the linear segment of the semilogarithmic curve. The total area under the curve (AUC) was calculated by adding together the partial areas: $AUC = AUD + AUC_{t-\infty}$. The AUC values were normalized by the actual dose given in the particular period. For calculation of the bioavailability, the buccal/oral AUC/dose value was divided by the intravenous AUC/dose value.

The individual plasma level-time curves were obtained. Small inter-individual variability was found after intravenous administration. After a very rapid initial decrease, the terminal elimination half-life of cladribine was about 10 hours. The mean total clearance proved to be 17 ml/min/kg. During buccal administration of the two formulations, the dissolution period was longer for the cladribine:γ-cyclodextrin complex compared to the cladribine:HP-β-cyclodextrin complex. Although the peak concentrations and the absorption profiles showed high inter-individual variability after both buccal and oral administrations, the total exposures (AUC) showed much lower variability. The oral bioavailability proved to be good: 50±3% and 45±5% for γ-cyclodextrin and hydroxypropyl-β-cyclodextrin complexes, respectively. The buccal bioavailability values were lower: 37±10% for the γ-cyclodextrin complex and 30±4.5% for the hydroxypropyl-β-cyclodextrin complex.

The results from further comparative dog pharmacokinetic studies of the γ-cyclodextrin complex and mixture are set forth in Table IX below. The "Oral Complex" column describes the results of absolute bioavailability of 5 mg cladribine in 2.5 g of γ-cyclodextrin; this is approximately 10 times the amount of cyclodextrin in a saturated complex with 5 mg cladribine. This preparation was the same as in the "Oral Mix" column, with the exception that the complex was preformed as opposed to only mixing the components. The results for the "Oral Mix" and "Oral Complex" are comparable, indicating that with such a large excess of cyclodextrin, a complex forms during dissolution, interfering with dissolution and exerting a negative impact on bioavailability. The same dogs and the same experimental method were used as before. These results show that the use of excess cyclodextrin is counter-productive, i.e., the saturated cladribine-cyclodextrin complex substantially free of cyclodextrin in excess of the minimum amount required to maintain substantially all of the cladribine in the complex provided both enhanced bioavailability and decreased interpatient variability.

TABLE IX

Bioavailability of 5 mg cladribine in 2.5 g γ-Cyclodextrin
Complex dose: mg cladribine/animal

| Dog | Buccal Tablet | Oral Tablet | Oral Mix 10x in Capsule[a] | Oral Complex 10x in Capsule[a] |
|---|---|---|---|---|
| PM01 | 30.0 | 51.9 | 35.3 | 39.5 |
| PM02 | 50.0 | 49.6 | 29.5 | 27.5 |
| PM03 | 50.6 | 52.6 | 27.4 | 32.6 |
| PM04 | 27.5 | 50.0 | 24.9 | 34.7 |
| PM05 | 29.9 | 17.0* | 36.1 | 12 |
| PM06 | 33.1 | 45.4 | 42.3 | 32.7 |
| Mean | 36.9 | 49.9 | 34.2 | 33.4 |
| S. D. | 10.6 | 2.8 | 6.8 | 4.3 |
| CV % | 29 | 6 | 20 | 1.3 |

*excluded from mean
[a] excess cyclodextrin, ≈10x that for the saturated complex. The total amount of cyclodextrin in these studies is ~2.5 gm with 5 mg cladribine.

The results of the foregoing pharmacokinetic studies are graphically represented in FIGS. 2-6.

Figure 2:
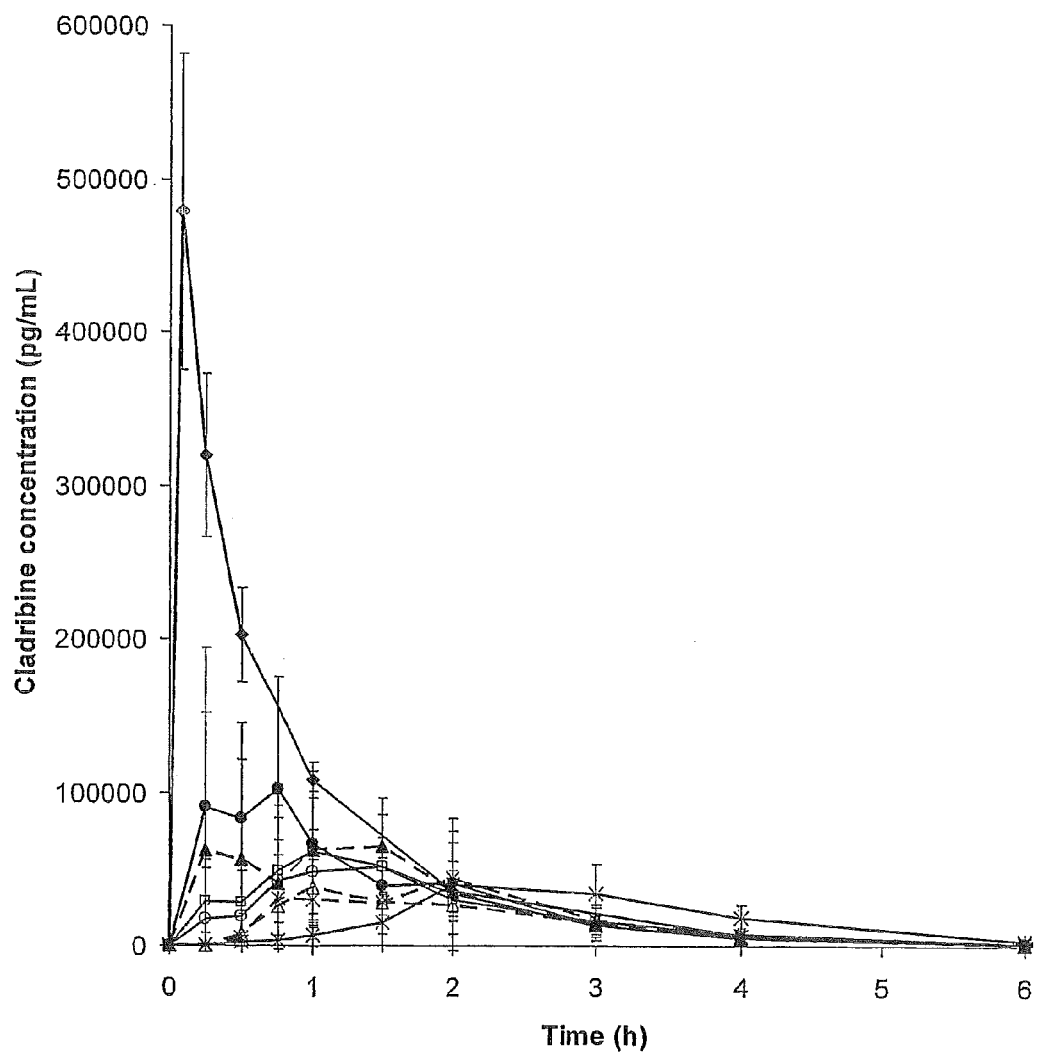
FIG. 2 shows plasma profiles for cladribine in dogs after administration of 5 mg single doses of cladribine with data showing the average concentration of cladribine in the plasma, in pg/ml, ±SD for 5-6 animals per group, plotted against time in hours, following administration of the following cladribine formulations: (◊) intravenous (i.v.) bolus; (*) saturated buccal cladribine γ-cyclodextrin complex; (x) saturated buccal cladribine-hydroxypropyl-β-cyclodextrin complex; (●) saturated oral cladribine-γ-cyclodextrin complex; (○) oral capsule of physical mixture of cladribine with ten times excess γ-cyclodextrin; (□) oral capsule of cladribine complex with ten times excess γ-cyclodextrin; (▲) saturated oral cladribine-hydroxypropyl-β-cyclodextrin complex; and (Δ) oral capsule of physical mixture of cladribine with ten times excess hydroxypropyl-β-cyclodextrin.

FIG. 2 shows the plasma profile for cladribine in dogs after administration of 5 mg single doses in the various formulations described above, where the data are the average±SD for 5-6 animals per group. The average drug concentration in pg/ml of plasma is plotted against time in hours. Although each test was conducted for a 48-hour period, only the first 6 hours were presented in the graphs; after 6 hours, most concentrations had returned to or near baseline and therefore are not shown in the graphs. Intravenous values (◇) are considered to give 100% bioavailability, and plasma levels for oral and buccal forms were compared thereto. The meanings of the symbols are given in the BRIEF DESCRIPTION OF THE DRAWINGS hereinabove. The buccal formulations of the saturated complexes with γ-cyclodextrin (*) and hydroxypropyl-β-cyclodextrin (x) were found to be less effective than the oral formulations in these tests, and this is readily seen in FIG. 2. The results for the five different oral formulations can be more readily seen by reference to FIGS. 3-5.

Figure 3:
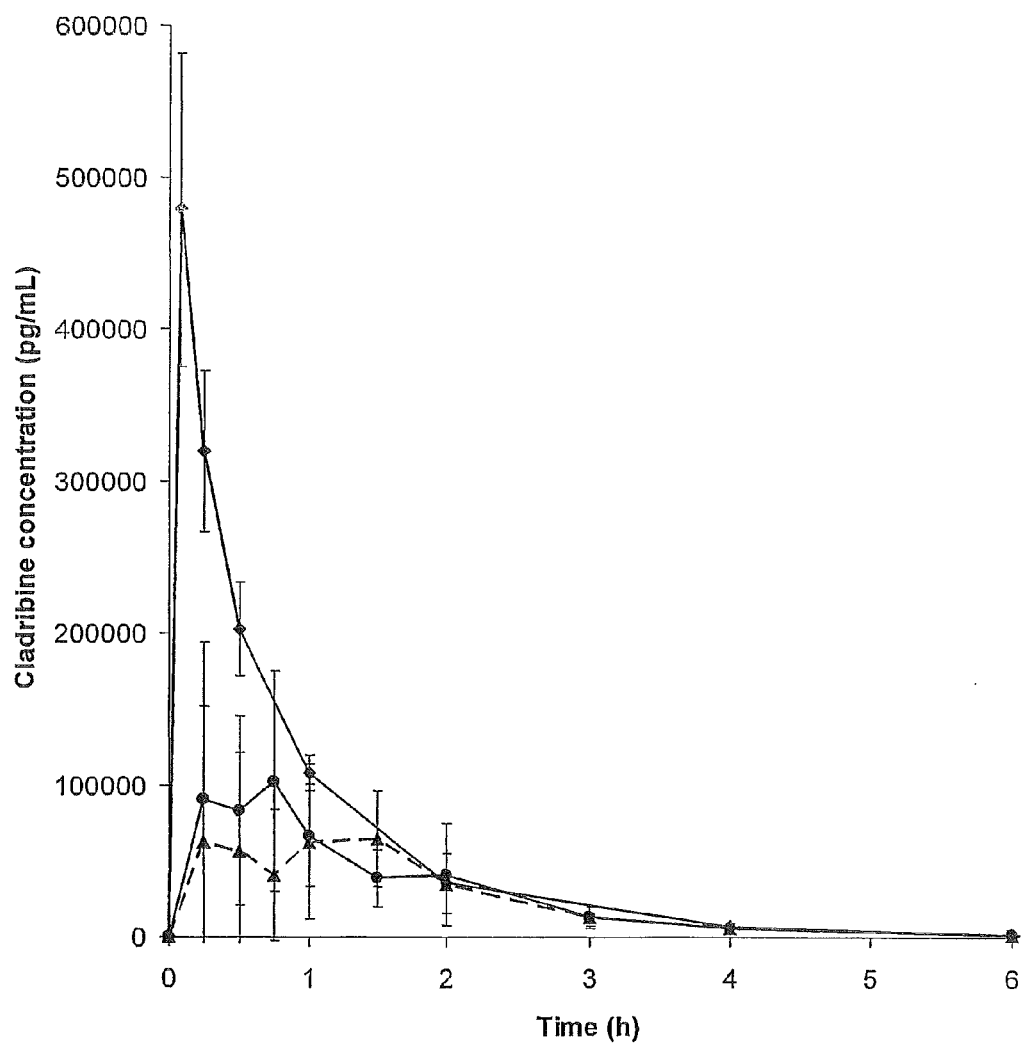
FIG. 3 represents a comparison of plasma profiles for cladribine in dogs after administration of 5 mg single doses of cladribine, with data showing the average concentration, in pg/mL, ±SD for 5-6 animals per group, plotted against time in hours, following administration of the following cladribine formulations: (♦) intravenous (i.v.) bolus, (●) saturated oral cladribine-γ-cyclodextrin complex, and (▲) saturated oral cladribine-hydroxypropyl-β-cyclodextrin complex.

FIG. 3 provides a comparison of the plasma profiles for the intravenous formulation (♦), the oral saturated cladribine-γ-cyclodextrin complex formulation (●) and the oral saturated cladribine-hydroxypropyl-β-cyclodextrin complex formulation (▲) shown in FIG. 2. Both of these oral formulations afforded desirable profiles.

Figure 4:
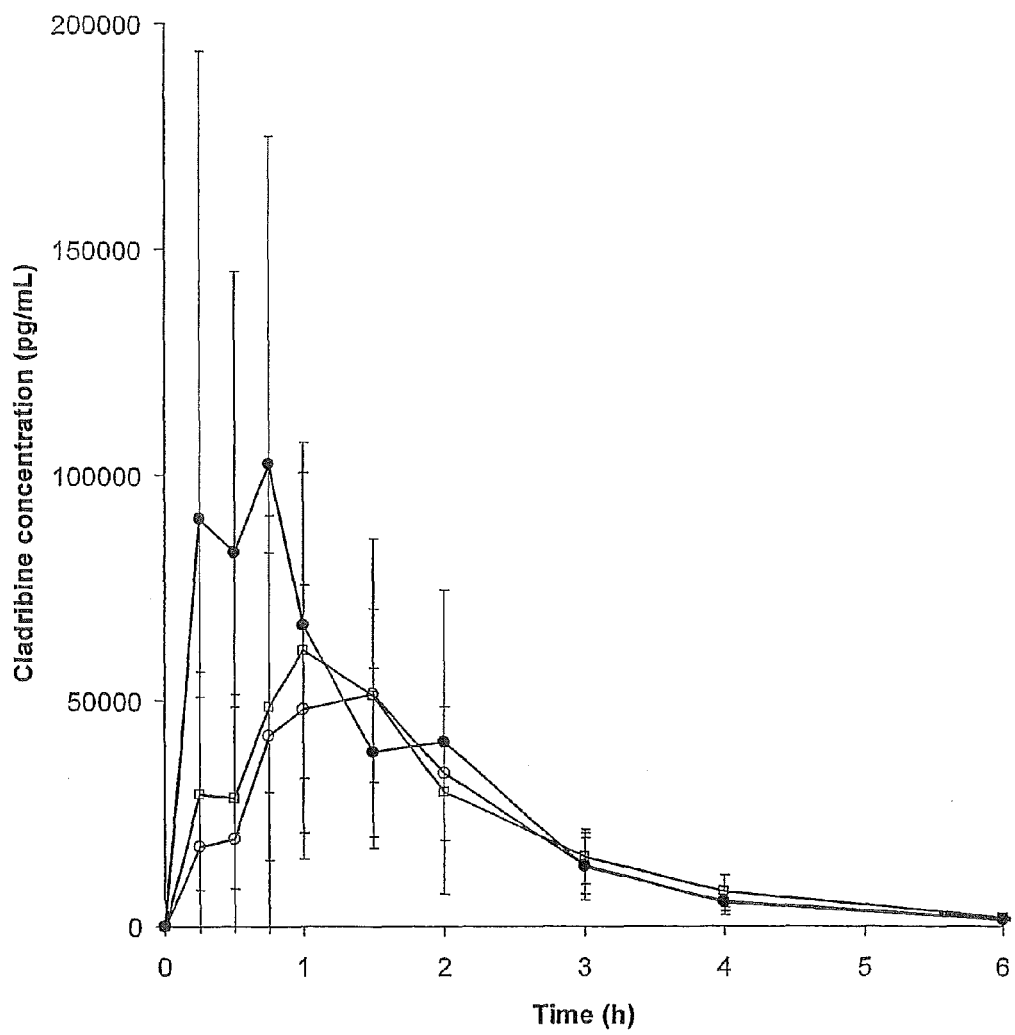
FIG. 4 represents a comparison of plasma profiles for cladribine in dogs after oral administration of 5 mg single doses of cladribine, with data showing the average concentration, in pg/mL, ±SD for 5-6 animals per group, plotted against time in hours, following administration of the following cladribine formulations: (●) saturated oral cladribine-γ-cyclodextrin complex; (○) oral capsule of physical mixture of cladribine with ten times excess γ-cyclodextrin; and (□) oral capsule of cladribine complex with ten times excess γ-cyclodextrin.

FIG. 4 provides a comparison of the plasma profiles for the oral saturated cladribine-γ-cyclodextrin complex formulation (●), the oral capsule of a physical mixture of cladribine with ten-times excess γ-cyclodextrin (○) and the oral capsule of the cladribine-γCD complex with ten times excess γ-cyclodextrin (□) shown in FIG. 2. Here it is apparent that excess cyclodextrin decreases the amount of cladribine in the plasma, particularly in the first hour after administration.

Figure 5:
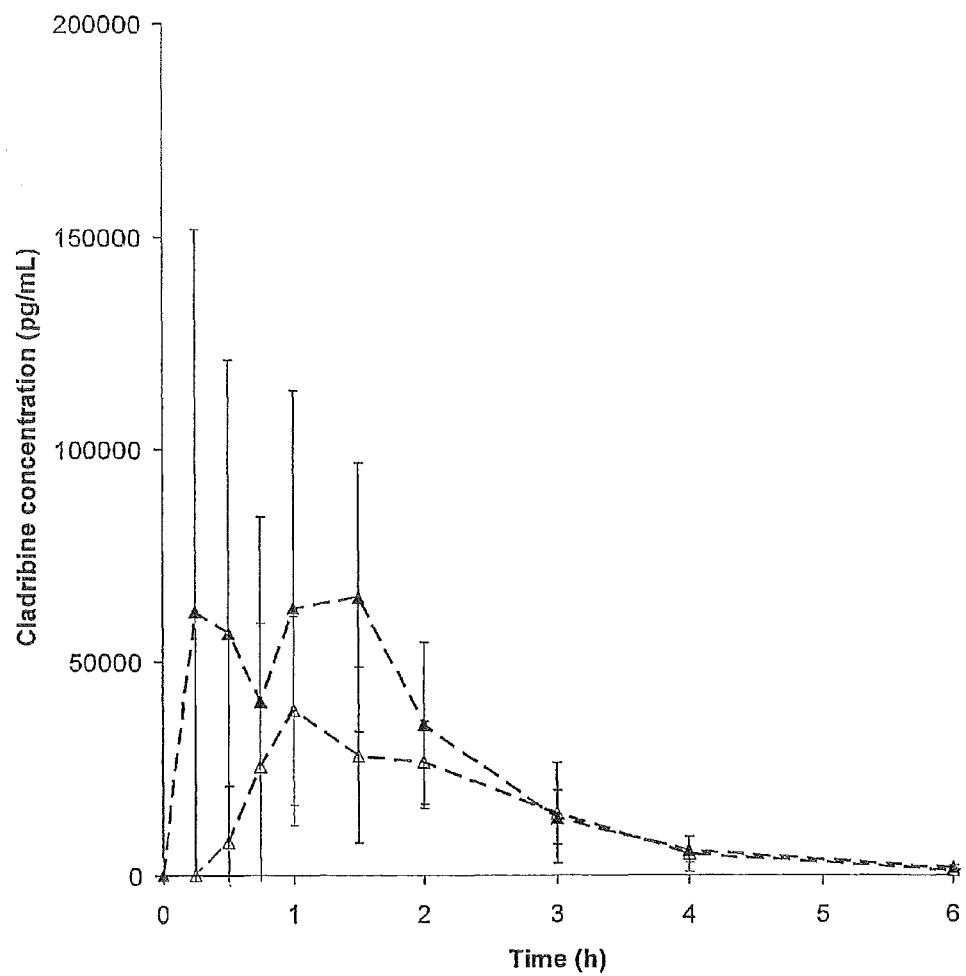
FIG. 5 represents a comparison of plasma profiles for cladribine in dogs after oral administration of 5 mg single doses of cladribine, with data showing the average concentration, in pg/mL, ±SD for 5-6 animals per group, plotted against time in hours, following administration of the following cladribine formulations: (▲) saturated oral cladribine-hydroxypropyl-β-cyclodextrin complex; and (Δ) oral capsule of physical mixture of cladribine with ten times excess hydroxypropyl-β-cyclodextrin.

FIG. 5 provides a comparison of the plasma profiles for the oral saturated hydroxypropyl-β-cyclodextrin complex formulation (▲) and the oral capsule of a physical mixture of cladribine with ten-times excess hydroxypropyl-β-cyclodextrin (Δ) shown in FIG. 2. Here it is again readily apparent that excess cyclodextrin decreases the amount of cladribine in the complex. In this case, the decrease is seen in the first two hours after administration.

Figure 6:
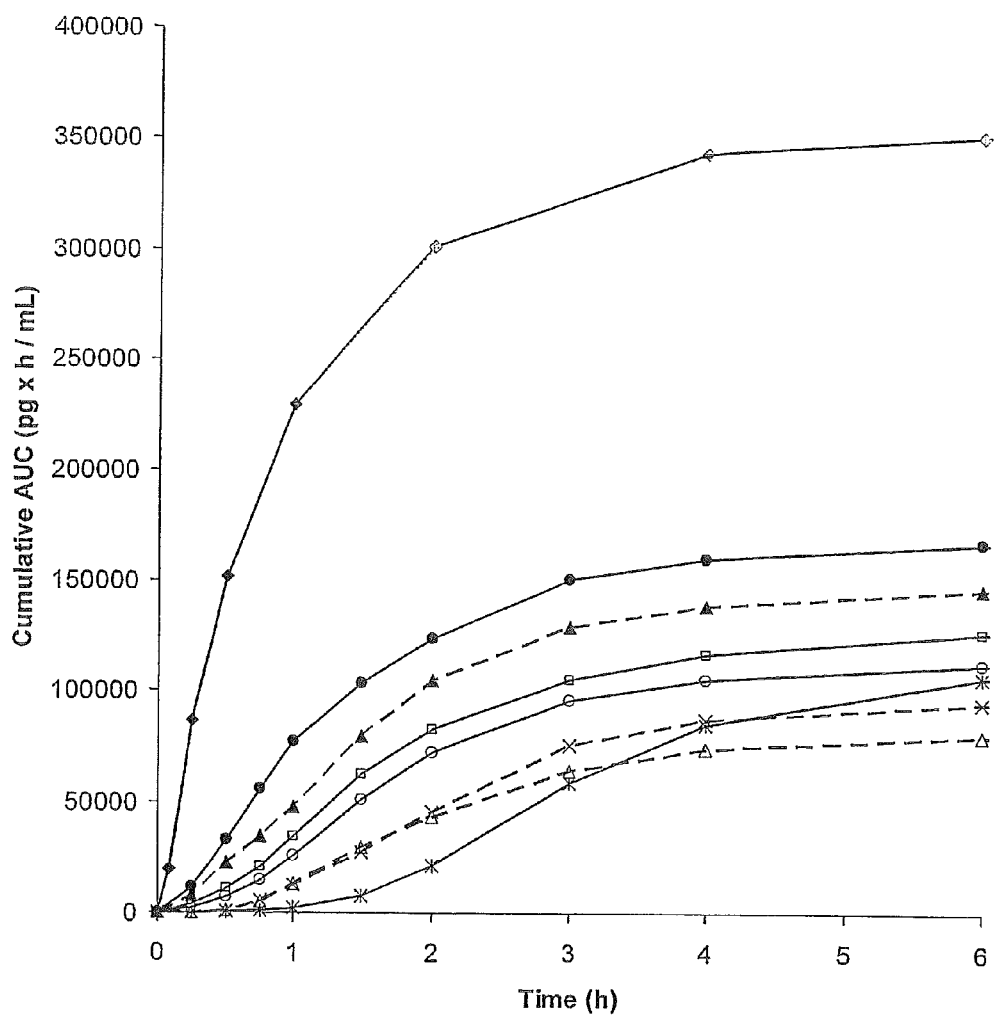
FIG. 6 illustrates the average cumulative area under the curve (AUC), in pg×h/mL, for cladribine in groups of 5-6 dogs, plotted against time in hours, after administration of each of the formulations described with reference to FIG. 2, where the symbols are as indicated in that paragraph.

FIG. 6 depicts the cumulative areas under the curves (AUCs) in pg xh/ml for the eight formulations shown in FIG. 2. Again, data are the average for 5-6 animals per group.

The figures thus graphically illustrate what is shown by the data in Tables III through IX, that the saturated cladribine-cyclodextrin complex, formulated as a solid oral or a transmucosal dosage form substantially free of cyclodextrin in excess of the minimum amount required to maintain substantially all of the cladribine in the complex, provides enhanced bioavailability with acceptable interpatient variability.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents thereof may be resorted to, falling within the scope of the invention claimed.

What is claimed is:

1. A pharmaceutical composition comprising a saturated cladribine-cyclodextrin complex formulated into a solid oral dosage form, said composition being substantially free of cyclodextrin in excess of the minimum amount required to maximize the amount of cladribine in the complex, or to maintain substantially all of the cladribine in the complex, wherein the cyclodextrin is γ-cyclodextrin, wherein the weight ratio of cladribine to γ-cyclodextrin is from about 1:35 to about 1:50 and wherein the complex comprises a 1:2 molar ratio cladribine:γ-cyclodextrin complex.

2. The composition according to claim 1, wherein the weight ratio of cladribine to γ-cyclodextrin is about 1:46.

3. The composition according to claim 1, wherein the approximate molar ratio of ciadribine to γ-cyclodextrin corresponds to a point located on the curve of a phase solubility diagram for saturated complexes of cladribine in varying concentrations of the cyclodextrin, said point being taken from the portion of the curve of the phase solubility diagram indicative of formation of a 1:2 molar ratio complex of cladribine:γ-cyclodextrin.

4. A method for enhancing the oral bioavailability of cladribine comprising administering to a subject in need thereof a pharmaceutical composition comprising a saturated cladribine-cyclodextrin complex formulated into a solid oral dosage form, said composition being substantially free of cyclodextrin in excess of the minimum amount required to maximize the amount of cladribine in the complex, or to maintain substantially all of the cladribine in the complex, wherein the cyclodextrin is γ-cyclodextrin, wherein the weight ratio of cladribine to γ-cyclodextrin is from about 1:35 to about 1:50, and wherein the complex comprises a 1:2 molar ratio cladribine: γ-cyclodextrin complex.

5. The method according to claim 4, wherein the weight ratio of cladribine to γ-cyclodextrin is about 1:46.

6. The method according to claim 4, wherein the approximate molar ratio of cladribine to γ-cyclodextrin corresponds to a point located on the curve of a phase solubility diagram for saturated complexes of cladribine in varying concentrations of the cyclodextrin, said point being taken from the portion of the curve of the phase solubility diagram indicative of formation of a 1:2 molar ratio complex of cladribine:γ-cyclodextrin.

7. A method for the treatment of symptoms of a cladribine-responsive condition selected from the group consisting of multiple sclerosis, rheumatoid arthritis and leukemia in a subject suffering from said symptoms comprising administering to said subject a pharmaceutical composition comprising a saturated cladribine-cyclodextrin complex formulated into a solid oral dosage form, said composition being substantially free of cyclodextrin in excess of the minimum amount required to maximize the amount of cladribine in the complex, or to maintain substantially all of the cladribine in the complex, wherein the cyclodextrin is γ-cyclodextrin, wherein the weight ratio of cladribine to γ-cyclodextrin is from about 1:35 to about 1:50, and wherein the complex comprises a 1:2 molar ratio cladribine: γ-cyclodextrin complex.

8. The method according to claim 7, wherein the cladribine-responsive condition is multiple sclerosis.

9. The method according to claim 7, wherein the weight ratio of cladribine to γ-cyclodextrin is about 1:46.

* * * * *